United States Patent
Abels et al.

(10) Patent No.: US 9,199,948 B2
(45) Date of Patent: Dec. 1, 2015

(54) 1,3-BENZOXAZOL-2(3H)-ONES AND THEIR USE AS MEDICAMENTS AND COSMETICS

(71) Applicant: DR. AUGUST WOLFF GMBH & CO. KG ARZNEIMITTEL, Bielefeld (DE)

(72) Inventors: Christoph Abels, Bielefeld (DE); Ulrich Knie, Bielefeld (DE); Michael Soeberdt, Bielefeld (DE)

(73) Assignee: Dr. August Wolff GMBH & Co. KG Arzneimittel, Bielefeld (DE)

( * ) Notice: Subject to any disclaimer, the term of this patent is extended or adjusted under 35 U.S.C. 154(b) by 0 days.

(21) Appl. No.: 14/401,989

(22) PCT Filed: May 21, 2013

(86) PCT No.: PCT/EP2013/001501
§ 371 (c)(1),
(2) Date: Nov. 18, 2014

(87) PCT Pub. No.: WO2013/174508
PCT Pub. Date: Nov. 28, 2013

(65) Prior Publication Data
US 2015/0111935 A1    Apr. 23, 2015

(30) Foreign Application Priority Data
May 21, 2012   (EP) .................................. 12168639

(51) Int. Cl.
| | |
|---|---|
| *C07D 263/58* | (2006.01) |
| *A61Q 19/00* | (2006.01) |
| *A61K 8/49* | (2006.01) |
| *A61Q 7/00* | (2006.01) |
| *A61Q 7/02* | (2006.01) |

(52) U.S. Cl.
CPC ............... *C07D 263/58* (2013.01); *A61K 8/49* (2013.01); *A61Q 7/00* (2013.01); *A61Q 7/02* (2013.01); *A61Q 19/00* (2013.01); *A61Q 19/007* (2013.01); *A61K 2800/10* (2013.01)

(58) Field of Classification Search
None
See application file for complete search history.

(56) References Cited

U.S. PATENT DOCUMENTS 7,816,376 B2 * 10/2010 Schadt ................. C07D 263/58
514/253.07
2005/0124627 A1    6/2005 Schadt et al.

FOREIGN PATENT DOCUMENTS

EP          0 249 407       12/1987
WO         2010 136 221     12/2010

OTHER PUBLICATIONS

DiMarzo, V., "Targeting the Endocannabinoid System: To Enhance or Reduce?" www.nature.com/reviews/drugdisc May 2008, vol. 7, pp. 438-455.
Leonti, M., Casu, L., Raduner, S., Cottiglia, F., Floris, C., Altmann, K., Gertsch, J., "Falcarinol is a Covalent Cannabinoid CB 1 Receptor Antagonist and Induces Pro-Allergic Effects in Skin" Biochemical Pharmacology—Biochem Pharmacol, 2010, vol. 79, No. 12, pp. 1815-1826.
Karsak, M., Gaffal, E., Date, R., Wang-Eckhardt, L., Rehnelt, J., Petrosino, S., Starowicz, K., Steuder, R., Schlicker, E., Cravatt, B., Mechoulam, R., Buettner, R., Werner, S., DiMarzo, V., Tuting, T., Zimmer, A., "Attenuation of Allergic Contact Dermatitis through the Endocannabinoid System" www.sciencemag.org, Jun. 8, 2007, vol. 316, pp. 1494-1497.
Ibrahim, M., Porreca, F., Lai, J., Albrecht, P., Rice, F., Khodorova, A., Davar, G., Makriyannis, A., Vanderah, T., Mata, H., Malán, T., "CB2 Cannabinoid Receptor Activation Produces Antinociception by Stimulating Peripheral Release of Endogenous Opiods" www.pnas.org, Feb. 22, 2005, vol. 102, No. 8, pp. 3093-3098.
Yates, M., Barker, E., "Inactivation and Biotransformation of the Endogeneous Cannabinoids Anandamide and 2-Arachidonoylglycerol" Molecular Pharmacology, 2009, vol. 78, No. 1, pp. 11-17.
International Search Report, WO 2013/174508, Nov. 28, 2013.

* cited by examiner

*Primary Examiner* — Kamal Saeed
(74) *Attorney, Agent, or Firm* — Daniel A. Thomson; Emerson Thomson Bennett

(57) ABSTRACT

The present invention relates to a novel class of 1,3-benzoxazol-2(3H)-ones and their use as a medicament, preferably as a dermatologic agent, and as a cosmetic. These novel compounds are particularly useful in treating and/or preventing inflammation, irritation, itching, pruritus, pain, oedema and/or pro-allergic or allergic conditions in a patient. Usually they are topically applied to the skin or mucosa in the form of a pharmaceutical or cosmetic composition comprising the compound and a pharmaceutically and/or cosmetically acceptable carrier.

18 Claims, No Drawings

1,3-BENZOXAZOL-2(3H)-ONES AND THEIR USE AS MEDICAMENTS AND COSMETICS

The present invention relates to a novel class of 1,3-benzoxazol-2(3H)-ones and their use as a medicament, preferably as a dermatologic agent, and as cosmetics. These novel compounds target the endocannabinoid system and are particularly useful in treating and/or preventing inflammation, irritation, itching, pruritus, pain, oedema, and/or pro-allergic or allergic conditions in a patient. Usually they are topically applied to the skin or mucosa of a mammal in the form of a pharmaceutical or cosmetic composition comprising the compound and a pharmaceutically and/or cosmetically acceptable carrier.

BACKGROUND OF THE INVENTION

The endocannabinoid system (ECS) comprises cannabinoid receptors ($CB_1$ and $CB_2$, TRPV1 and potentially also GPR55), arachidonic acid-derived ligands, and their regulatory enzymes. The importance of the endocannabinoid system in peripheral tissues has been demonstrated in numerous recent studies (Di Marzo V. *Targeting the endocannabinoid system: to enhance or reduce?* Nat Rev Drug Discov. 2008 May; 7(5):438-55). Whereas the activation of the peripheral endocannabinoid system is often associated with anti-inflammatory and immunosuppressive effects, in the skin the role of the ECS is more complex. $CB_2$ receptor activation has been shown to trigger endorphins that locally act analgesic (Ibrahim M M, Porreca F, Lai J, Albrecht P J, Rice F L, Khodorova A, Davar G, Makriyannis A, Vanderah T W, Mata H P, Malan T P Jr. *CB2 cannabinoid receptor activation produces antinociception by stimulating peripheral release of endogenous opioids.* Proc Natl Acad Sci USA. 2005 Feb. 22; 102(8):3093-8). Studying CB knockout mice, it has been observed that the ECS and the $CB_1$ receptor can inhibit the pathogenesis of allergic contact dermatitis (Karsak M, Gaffal E, Date R, Wang-Eckhardt L, Rehnelt J, Petrosino S, Starowicz K, Steuder R, Schlicker E, Cravatt B, Mechoulam R, Buettner R, Werner S, Di Marzo V, Tilting T, Zimmer A. *Attenuation of allergic contact dermatitis through the endocannabinoid system.* Science. 2007 Jun. 8; 316(5830):1494-7). Interestingly, in this study it was shown that inhibitors of anandamide degradation via fatty acid amide hydrolase (FAAH) could be a promising therapeutic strategy to treat different forms of dermatitis. Overall, the endocannabinoid system in the skin is present, both $CB_1$ and $CB_2$ receptors have been detected in keratinocytes and fibroblasts and the endocannabinoids are released in the skin where they seem to regulate multiple signals involved in inflammation. Anandamide exerts potent anti-inflammatory and anti-allergic effects (Leonti M, Casu L, Raduner S, Cottiglia F, Floris C, Altmann K H, Gertsch J. Falcarinol is a covalent cannabinoid $CB_1$ receptor antagonists and induces pro-allergic effects in skin. Biochem. Pharmacol. 2010, 79: 1815-1826). Moreover, anandamide reuptake inhibitors have been shown to exert a number of beneficial effects including neuropathic and peripheral pain (Yates M L, Baker E L. Inactivation and Biotransformation of the endogenous cannabinoids anandamide and 2-arachidonoyl glycerol. Mol. Pharmacol. 2009, 76: 11-17). However, the mechanisms underlying are not yet fully understood and there still remain numerous questions to be answered.

WO2010/136221 discloses dodeca-2E,4E-diene amides and their use as medicaments and cosmetics.

Thus, the claimed class of 1,3-benzoxazol-2(3H)-ones of the present invention is not disclosed in the prior art, let alone to be suitable and active in the treatment and prevention of skin disorders.

Further, even if a large number of dermatologic agents and preparations is known in the prior art for treating any kinds of skin discomfort, there is a still a strong demand to find new active agents being more effective, requiring even reduced amounts to be applied, and having less undesirable side-effects.

Thus, the object underlying the present invention is the provision of new compounds suitable as medicaments. It is a further object of the present invention to provide for new compounds suitable as dermatologic agents for treating and preventing several conditions including inflammation, irritation, itching, pruritus, pain, oedema, and/or pro-allergic or allergic conditions etc., particularly of the skin and mucosa of a mammal, which compounds are more effective, require reduced amounts of active ingredient as compared to prior art compounds and, and have less undesirable side-effects.

SUMMARY OF THE INVENTION

The objects as mentioned above have surprisingly been solved in accordance with the present invention. Thus, the present invention relates to specific 1,3-benzoxazol-2(3H)-ones according to formula (1) below.

formula (1)

The compounds according to formula (1) are alternative solutions to the same problem and have not been obvious for the skilled person.

In formula (1) the residue $R^1$ is selected from the group consisting of $-(CH_2)_nN(R^4)C(O)R^5$ and $-C(O)NR^4R^6$. Preferably $R^1$ is $-(CH_2)_nN(R^4)C(O)R^5$.

In formula (1) the residue $R^2$ is selected from the group consisting of hydrogen; $-C_{1-6}$alkyl, optionally substituted with one or more substituents selected from halogen, OH, $OC_{1-6}$alkyl, $OC_{3-7}$cycloalkyl; $-C_{3-7}$cycloalkyl, optionally substituted with one or more substituents selected from halogen, OH, $OC_{1-6}$alkyl, $OC_{3-7}$cycloalkyl; $-(C_{3-7}$cycloalkyl)-$C_{1-6}$-alkyl, optionally substituted with one or more substituents selected from halogen, OH, $OC_{1-6}$alkyl, $OC_{3-7}$ cycloalkyl. While the above mentioned optional substituents are preferable according to the present invention, other substituents as mentioned below in the description are suitable according to the present invention as well.

In formula (1) the residue $R^3$ is selected from the group consisting of hydrogen, halogen, hydroxy, methoxy or —CN.

In formula (1) the residue $R^4$ is selected from the group consisting of hydrogen or $C_{1-6}$-alkyl.

In formula (1) the residue $R^5$ is selected from the group consisting of $C_{8-15}$alkyl, $C_{8-15}$alkenyl, $C_{8-15}$alkinyl, ($C_{6-10}$aryl)-$C_{6-10}$alkyl, ($C_{6-10}$aryl)-$C_{6-10}$alkenyl, and ($C_{6-10}$aryl)-$C_{6-10}$alkinyl. In all of these aryl containing groups aryl may be substituted by one or more of the substituents as mentioned below in the present description.

In formula (1) the residue $R^6$ is selected from the group consisting of $C_{9-16}$alkyl, $C_{9-16}$alkenyl, $C_{9-16}$alkinyl, ($C_{6-10}$aryl)-$C_{7-11}$alkyl, ($C_{6-10}$aryl)-$C_{7-11}$alkenyl, and ($C_{6-10}$aryl)-

$C_{7-11}$alkinyl. In all of these aryl containing groups aryl may be substituted by one or more of the substituents as mentioned below in the present description.

In formula (1) n is 0, 1, or 2, preferably 0 or 1, more preferably 0.

Preferably, the compounds according to the present invention are those, wherein in formula (1) $R^1$ is —$(CH_2)_nN(R^4)C(O)R^5$ with n being 0 or 1, preferably 0; $R^2$ is hydrogen or $C_{1-6}$alkyl, optionally substituted with one or more substituents selected from halogen, OH, $OC_{1-6}$alkyl, $OC_{3-7}$cycloalkyl; $R^3$ is hydrogen or halogen, preferably hydrogen; $R^4$ is hydrogen; and $R^5$ is selected from $C_{8-15}$alkyl, $C_{8-15}$alkenyl, $(C_{6-10}$aryl)-$C_{6-10}$alkyl, and $(C_{6-10}$aryl)-$C_{6-10}$alkenyl. In these definitions aryl is optionally substituted with one or more substituents as mentioned hereinbelow.

Preferably, the compounds according to the present invention are those, wherein in formula (1) $R^1$ is —$C(O)NR^4R^6$; $R^2$ is hydrogen or $C_{1-6}$alkyl, optionally substituted with one or more substituents selected from halogen, OH, $OC_{1-6}$alkyl, $OC_{3-7}$cycloalkyl; $R^3$ is hydrogen or halogen, preferably hydrogen; $R^4$ is hydrogen; and $R^6$ is selected from $C_{9-16}$alkyl, $C_{9-16}$alkenyl, $(C_{6-10}$aryl)-$C_{7-11}$alkyl, and $(C_{6-10}$aryl)-$C_{7-11}$alkenyl, wherein aryl is optionally substituted with one or more substituents as mentioned hereinbelow.

More preferably, the compounds according to the present invention are those, wherein in formula (1) $R^1$ is —$(CH_2)_nN(R^4)C(O)R^5$ with n being 0; $R^2$ is hydrogen or methyl; $R^3$ is hydrogen; $R^4$ is hydrogen; and $R^5$ is selected from $C_{8-15}$alkyl, $C_{8-15}$alkenyl (wherein alkenyl contains 1, 2, or 3 double bonds), $(C_{6-10}$aryl)-$C_{6-10}$alkyl, and $(C_{6-10}$aryl)-$C_{6-10}$alkenyl (wherein alkenyl contains 1 or 2 double bonds).

Even preferably, the compounds according to the present invention are those, wherein in formula (1) $R^1$ is —$C(O)NR^4R^6$; $R^2$ is hydrogen or methyl; $R^3$ is hydrogen; $R^4$ is hydrogen; and $R^6$ is selected from $C_{9-16}$alkyl, $C_{9-16}$alkenyl (wherein alkenyl contains 1, 2, or 3 double bonds), $(C_{6-10}$aryl)-$C_{7-11}$alkyl, and $(C_{6-10}$aryl)-$C_{7-11}$alkenyl (wherein alkenyl contains 1 or 2 double bonds).

More preferably, the compounds according to the present invention are those, wherein in formula (1) $R^1$ is —$(CH_2)_nN(R^4)C(O)R^5$ with n being 0; $R^2$ is hydrogen or methyl; $R^3$ is hydrogen; $R^4$ is hydrogen; and $R^5$ is selected from $C_{8-12}$alkyl, $C_{8-12}$alkenyl (wherein alkenyl contains 2 double bonds), $(C_{6-10}$aryl)-$C_{6-8}$alkyl, and $(C_{6-10}$aryl)-$C_{6-8}$alkenyl (wherein alkenyl contains 2 double bonds).

In a particularly preferred embodiment of the present invention the compound according to formula (1) contains $R^1$ being —$(CH_2)_nN(R^4)C(O)R^5$ with n being 0, $R^2$ being hydrogen or methyl, and $R^3$ being hydrogen. In the definition of $R^1$ herein, $R^4$ is hydrogen and $R^5$ is selected from $C_{8-12}$alkyl, $C_{8-12}$alkenyl containing a (2E,4E)-diene moiety as the unsaturation, $(C_{6-10}$aryl)-$C_{6-8}$alkyl, and $(C_{6-10}$aryl)-$C_{6-8}$alkenyl containing a (2E,4E)-diene moiety as the unsaturation in the alkenyl group thereof.

Also preferably, the compounds according to the present invention are those, wherein in formula (1) $R^1$ is —$C(O)NR^4R^6$; $R^2$ is hydrogen or methyl; $R^3$ is hydrogen; $R^4$ is hydrogen; and $R^6$ is selected from $C_{9-13}$alkyl, $C_{9-13}$alkenyl (wherein alkenyl contains 2 double bonds), $(C_{6-10}$aryl)-$C_{7-9}$alkyl, and $(C_{6-10}$aryl)-$C_{7-9}$alkenyl (wherein alkenyl contains 2 double bonds).

In another particularly preferred embodiment of the present invention the compound according to formula (1) contains $R^1$ being —$C(O)NR^4R^6$, $R^2$ being hydrogen or methyl, and $R^3$ being hydrogen. In the definition of $R^1$ herein, $R^4$ is hydrogen and $R^6$ is selected from $C_{9-13}$alkyl, $C_{9-13}$alkenyl containing a (2E,4E)-diene moiety as the unsaturation, $(C_{6-10}$aryl)-$C_{7-9}$alkyl, and $(C_{6-10}$aryl)-$C_{7-9}$alkenyl containing a (2E,4E)-diene moiety as the unsaturation in the alkenyl group thereof.

Moreover, the present invention relates to the use of these compounds as a medicament, preferably a dermatologic agent, and as a cosmetic. The compounds are effective in the treatment and/or prevention of inflammation, irritation, itching, pruritus, pain, oedema, and/or pro-allergic or allergic conditions, particularly of the skin and mucosa of a mammal. Further conditions include hair growth (e.g. forms of alopecia, effluvium) and sebaceous gland disorders (e.g. acne, seborrhea), benign and malignant skin tumors, hyperproliferative skin diseases (e.g. psoriasis), excessive hair growth (e.g. hirsutism), different forms of dermatitis, dry skin conditions, and systemic sclerosis (*scleroderma*).

DETAILED DESCRIPTION OF THE INVENTION

In accordance with the present invention the applicant has developed the new 1,3-benzoxazol-2(3H)-ones as defined in formula (1) and has surprisingly found out that these compounds can effectively be used as a medicament, preferably as a dermatologic agent, and as a cosmetic due to their lipophilic nature. The conditions and diseases to be treated are particularly inflammation, itching, pruritus, irritation, pain, oedema, and/or pro-allergic or allergic conditions. The compounds turned out to be effective not only in the treatment but also in the prevention of the above mentioned conditions. The conditions also comprise inflammatory reactions and irritation of skin and mucosa of a mammal, preferably of a human, e.g. caused by environmental stress and influences, such as UV irradiation, toxic substances, and allergens in general. Thus, the compounds have shown to effectively reduce several kinds of skin and mucosa discomforts as mentioned above. In particular, they have shown to provide for analgesic and antipruritic properties.

Without intending to be bound by any theory the applicant believes that the reason for the activity of the 1,3-benzoxazol-2(3H)-ones of the present invention is based on their function as modulators of the endocannabinoid system. In this respect it is known that the endocannabinoids N-arachidonoylethanolamide (Anandamide, AEA) and 2-arachidonoylglycerol (2-AG) bind to G-protein-coupled $CB_1$ and $CB_2$ cannabinoid receptors. The $CB_1$ receptor is primarily (but not exclusively) expressed in neurons, the $CB_2$ receptor is mainly present in immunocytes, such as monocytes (splenocytes), macrophages, B cells, but also in astroglial cells. In the skin, CB receptors, in particular the $CB_2$ receptor, are expressed in keratinocytes and fibroblasts. Upon CB receptor activation, endocannabinoids are actively transported through the cell membrane and degraded. The metabolic enzymes fatty acid amide hydrolase (FAAH) and monoacyl glycerol lipase (MAGL) are responsible for the hydrolysis of AEA and 2-AG, respectively, thus leading to inactivation of these signaling molecules. While activation of the $CB_1$ receptor has been shown to mediate distinct neurophysiological effects, modulation of the $CB_2$ receptor by both agonists and inverse agonists is known to interfere with different inflammatory processes. $CB_2$ receptor activation can lead to anti-inflammatory effects in vivo and $CB_2$ receptor modulation has been implicated in the pathophysiology of a number of diseases, including chronic pain, inflammation of the gastrointestinal tract, osteoporosis, and liver diseases. Plants employ structurally similar lipid signaling molecules as animals to process cellular information, including endocannabinoid-like fatty acid derivatives. Since plants do not generally synthesize arachidonic acid, different N-acylethanolamines like e.g. N-palmitoylethanolamide are produced in plants and these lipids have also been shown to act on proteins directly or indirectly associated with the endocannabinoid system (ECS) in animals and humans, such as FAAH, the transient receptor potential vanilloid receptor (TRPV1) or the newly postulated cannabinoid receptor GPR55.

Thus, in accordance with the present invention it has been found that the 1,3-benzoxazol-2(3H)-ones of formula (1) show a significant functional interference with the ECS which is assumed to be a reason for their pharmacological activity. In particular, the claimed 1,3-benzoxazol-2(3H)-ones inhibit FAAH or AEA re-uptake. In addition, some compounds of the invention inhibit FAAH in addition to AEA re-uptake. In other words, these compounds inhibit AEA re-uptake or FAAH activity or both without effecting $CB_1$ and $CB_2$ receptors.

If not described in a different way herein, the employed terms for defining/describing in formula (1) the respective groups R (i.e. $R^1$ to $R^6$) including their substituents, if any, in accordance with the present invention have the meaning as described below:

Alkyl is a straight chain or branched alkyl having 1, 2, 3, 4, 5 or 6 carbon atoms, such as methyl, ethyl, n-propyl, isopropyl, n-butyl, isobutyl, tert-butyl, n-pentyl, isopentyl, neopentyl, or hexyl.

Alkenyl is a straight chain or branched alkyl having 2, 3, 4, 5 or 6 carbon atoms and one to three double bonds, preferably one or two double bonds, most preferably one double bond. Preferred examples of a $C_{2-6}$alkenyl group are ethenyl, prop-1-enyl, pro-2-enyl, isoprop-1-enyl, n-but-1-enyl, n-but-2-enyl, n-but-3-enyl, isobut-1-enyl, isobut-2-enyl, n-pent-1-enyl, n-pent-2-enyl, n-pent-3-enyl, n-pent-4-enyl, n-pent-1,3-enyl, isopent-1-enyl, isopent-2-enyl, neopent-1-enyl, n-hex-1-enyl, n-hex-2-enyl, n-hex-3-enyl, n-hex-4-enyl, n-hex-5-enyl, n-hex-1,3-enyl, n-hex-2,4-enyl, n-hex-3,5-enyl, and n-hex-1,3,5-enyl. More preferred examples of a $C_{2-6}$alkenyl group are ethenyl and prop-1-enyl.

Alkinyl is a straight chain or branched alkyl having 2, 3, 4, 5 or 6 carbon atoms and one to three triple bonds, preferably one or two triple bonds, most preferably one triple bond. Preferred examples of a $C_{2-6}$alkinyl group are ethinyl, prop-1-inyl, pro-2-inyl, n-but-1-inyl, n-but-2-inyl, n-but-3-inyl, n-pent-1-inyl, n-pent-2-inyl, n-pent-3-inyl, n-pent-4-inyl, n-pent-1,3-inyl, isopent-1-inyl, neopent-1-inyl, n-hex-1-inyl, n-hex-2-inyl, n-hex-3-inyl, n-hex-4-inyl, n-hex-5-inyl, n-hex-1,3-inyl, n-hex-2,4-inyl, n-hex-3,5-inyl, and n-hex-1,3,5-inyl. More preferred examples of a $C_{2-4}$alkinyl group are ethinyl and prop-1-inyl.

Cycloalkyl is an alkyl ring having 3, 4, 5, 6 or 7 carbon atoms at the most, such as cyclopropyl, cyclobutyl, cyclopentyl, cyclohexyl or cycloheptyl, more preferably 3, 4, 5 or 6 carbon atoms.

Rings are saturated or mono- to polyunsaturated carbon ring systems which may include one or more heteroatoms, such as O, N, S, and/or P. Preferred are 5- or 6-membered rings. Rings particularly include aryl and heteroaryl rings, which may be fused aromatic rings.

Aryl is an aromatic moiety having 6 to 20 carbon atoms, preferably 6 to 10 carbon atoms, and includes fused aromatic rings. Most preferred is phenyl.

Heteroaryl is an aromatic moiety having 1, 2, 3, 4, 5, 6, 7, 8 or 9 carbon atoms and at least one heteroatom selected from O, N and/or S. Preferably, heteroaryl comprises at most 10 ring atoms (including carbon and heteroatoms) and is preferably selected from thienyl, pyrrolyl, imidazolyl, pyrazolyl, pyridyl, pyrazinyl, pyrimidinyl, pyridazinyl, thiazolyl, oxazolyl, isothiazolyl, isoxazolyl, furanyl, oxadiazolyl, thiadiazolyl, tetrazolyl and indazolyl, more preferably from thienyl, furanyl, imidazolyl, pyridyl, thiazolyl, oxazolyl, oxadiazolyl, thiadiazolyl, tetrazolyl and pyrimidinyl.

Heterocyclyl is a saturated or unsaturated ring containing at least one heteroatom selected from O, N and/or S and 1, 2, 3, 4, 5, 6 or 7 carbon atoms. Preferably, heterocyclyl comprises at most 11 ring atoms (including carbon and heteroatoms) and more preferably is a 4 to 8-membered ring and even more preferably is selected from tetrahydrofuranyl, azetidinyl, pyrrolidinyl, piperidinyl, pyranyl, morpholinyl, thiazolinyl, dioxanyl, dioxolanyl, and thiomorpholinyl, more preferably from piperidinyl, thiazolinyl, dioxanyl, dioxolanyl, and pyrrolidinyl.

Halogen is a halogen atom selected from F, Cl, Br and I, preferably from F, Cl and Br.

The compounds of the present invention contain the 1,3-benzoxazol-2(3H)-one basic structure represented by the following formula (1).

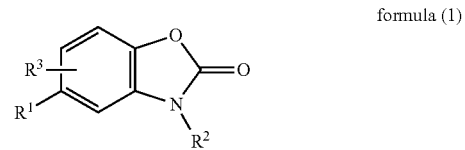

formula (1)

In the compounds according to formula (1) the essential feature for achieving the endocannabinoid system modulating/targeting activity is believed to be the specific definition of the $R^1$ residue, namely being either —$(CH_2)_nN(R^4)C(O)R^5$ (n being 0, 1, or 2, preferably 0 or 1, more preferably 0) or —$C(O)NR^4R^6$.

For both of the above definitions of $R^1$ and, moreover, independently of each other, the following definitions of $R^2$ to $R^6$ apply according to the present invention:

$R^2$ is selected from the group consisting of hydrogen; —$C_{1-6}$alkyl, such as methyl, ethyl, n- or i-propyl, n- or i-butyl, n- or i-pentyl, n- or i-hexyl, each optionally substituted with one or more substituents selected from halogen, OH, $OC_{1-6}$alkyl, —$OC_{3-7}$cycloalkyl; —$C_{3-7}$cycloalkyl, optionally substituted with one or more substituents selected from halogen, OH, $OC_{1-6}$alkyl, $OC_{3-7}$cycloalkyl; —($C_{3-7}$cycloalkyl)-$C_{1-6}$-alkyl, optionally substituted with one or more substituents selected from halogen, OH, $OC_{1-6}$alkyl, $OC_{3-7}$cycloalkyl. Preferably $R^2$ is hydrogen or $C_{1-6}$alkyl, optionally substituted with one or more substituents selected from halogen, OH, $OC_{1-6}$alkyl, $OC_{3-7}$cycloalkyl. More preferably, $R^2$ is hydrogen or methyl, particularly hydrogen.

$R^3$ is selected from the group consisting of hydrogen, halogen, hydroxy, methoxy or —CN. Preferably $R^3$ is hydrogen or halogen, more preferably hydrogen. The compounds according to formula (I) contain three $R^3$ groups that can be the same or different. Most preferably all of them are hydrogen.

$R^4$ is selected from the group consisting of hydrogen or $C_{1-6}$-alkyl, such as methyl, ethyl, n- or i-propyl, n- or i-butyl, n- or i-pentyl, n- or i-hexyl. Preferably $R^4$ is hydrogen or methyl, more preferably hydrogen.

$R^5$ is selected from the group consisting of $C_{8-15}$alkyl, $C_{8-15}$alkenyl, $C_{8-15}$alkinyl, ($C_{6-10}$aryl)-$C_{6-10}$alkyl, ($C_{6-10}$aryl)-$C_{6-10}$alkenyl, and ($C_{6-10}$aryl)-$C_{6-10}$alkinyl. In all of these aryl containing groups aryl may be substituted by one or more of the substituents as mentioned below in the present description. Preferably $R^5$ is selected from $C_{8-15}$alkyl, $C_{8-15}$alkenyl, ($C_{6-10}$aryl)-$C_{6-10}$alkyl, and ($C_{6-10}$aryl)-$C_{6-10}$ alkenyl. More preferably, $R^5$ is selected from $C_{8-15}$alkyl, $C_{8-15}$alkenyl (wherein alkenyl contains 1, 2, or 3, preferably 2 double bonds), $(C_{6-10}$aryl$)$-$C_{6-10}$alkyl, and $(C_{6-10}$aryl$)$-$C_{6-10}$alkenyl (wherein alkenyl contains 1 or 2, preferably 2 double bonds). Most preferably, $R^5$ is selected from $C_{8-12}$alkyl, $C_{8-12}$alkenyl containing a (2E,4E)-diene moiety as the unsaturation, $(C_{6-10}$aryl$)$-$C_{6-8}$alkyl, and $(C_{6-10}$aryl$)$-$C_{6-8}$alkenyl containing a (2E,4E)-diene moiety as the unsaturation in the alkenyl group thereof.

$R^6$ is selected from the group consisting of $C_{9-16}$alkyl, $C_{9-16}$alkenyl, $C_{9-16}$alkinyl, $(C_{6-10}$aryl$)$-$C_{7-11}$alkyl, $(C_{6-10}$aryl$)$-$C_{7-11}$alkenyl, and $(C_{6-10}$aryl$)$-$C_{7-11}$alkinyl. In all of these aryl containing groups aryl may be substituted by one or more of the substituents as mentioned below in the present description. Preferably, $R^6$ is selected from $C_{9-16}$alkyl, $C_{9-16}$alkenyl, $(C_{6-10}$aryl$)$-$C_{7-11}$alkyl, and $(C_{6-10}$aryl$)$-$C_{7-11}$alkenyl. More preferably, $R^6$ is selected from $C_{9-16}$alkyl, $C_{9-16}$ alkenyl (wherein alkenyl contains 1, 2, or 3, preferably 2 double bonds), $(C_{6-10}$aryl$)$-$C_{7-11}$alkyl, and $(C_{6-10}$aryl$)$-$C_{7-11}$alkenyl (wherein alkenyl contains 1 or 2, preferably 2 double bonds). Most preferably, $R^6$ is selected from $C_{9-13}$alkyl, $C_{9-13}$alkenyl containing a (2E,4E)-diene moiety as the unsaturation, $(C_{6-10}$aryl$)$-$C_{7-9}$alkyl, and $(C_{1-10}$aryl$)$-$C_{7-9}$alkenyl containing a (2E,4E)-diene moiety as the unsaturation in the alkenyl group thereof.

Specifically, in case $R^1$ is —$(CH_2)_n N(R^4)C(O)R^5$ with n=0, $R^5$ may not be a linear $C_{11}$ chain with a (2E,4E)-diene moiety.

Similarly, in case $R^1$ is —$C(O)NR^4R^6$ as defined herein, $R^6$ may not contain a (2E,4E)-diene moiety, or $R^6$ may not contain a linear dodeca-(2E,4E)-diene, aryl-hexa-(2E,4E)-diene, aryl-hepta-(2E,4E)-diene, and/or aryl-octa-(2E,4E)-diene moiety.

All possible combinations of the definitions of $R^1$ to $R^6$ in formula (1) included in the lists above should be understood as being directly and unambiguously disclosed according to the present invention.

In general, substituents of the carbon chains and rings in accordance with the invention are halogens, preferably F, Cl, Br and I, $C_{1-10}$alkyl, $C_{1-10}$alkoxy, $C_{6-20}$aryl, hydroxyl, —SH, —$SO_3H$, amine groups, —COOH, COOR', wherein R' is a $C_{1-10}$alkyl or an alkali metal, CONHR'', and CON(R'')$_2$, wherein R'' is a $C_{1-10}$alkyl. In general, particularly preferred alkyl and alkoxy groups used as substituents in accordance with the present invention as described herein are $C_{1-6}$alkyl and $C_{1-6}$alkoxy groups, more preferably methyl, ethyl, n-propyl, i-propyl, n-butyl, i-butyl, n-pentyl, iso-pentyl, methoxy, ethoxy, n-propoxy, i-propoxy, n-butoxy, i-butoxy, n-pentoxy, iso-pentoxy. Similarly, particularly preferred aryl groups are $C_{6-10}$aryl groups, most preferably phenyl. Suitable substituents are also selected from alkenyl, alkinyl, cycloalkyl, heteroaryl, heterocyclyl as defined herein.

In particularly preferred embodiments of the present invention the compounds are according to the following formula (2):

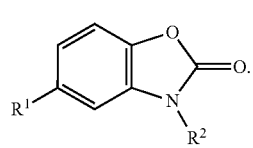

formula (2)

In formula (2) $R^2$ is preferably either hydrogen or methyl, more preferably hydrogen. Further, $R^1$ is as defined above.

According to the present invention, in compounds of formulae (1) and/or (2), $R^1$ may also be selected from the group consisting of the following radicals (which may be substituted by substituent groups as defined herein):

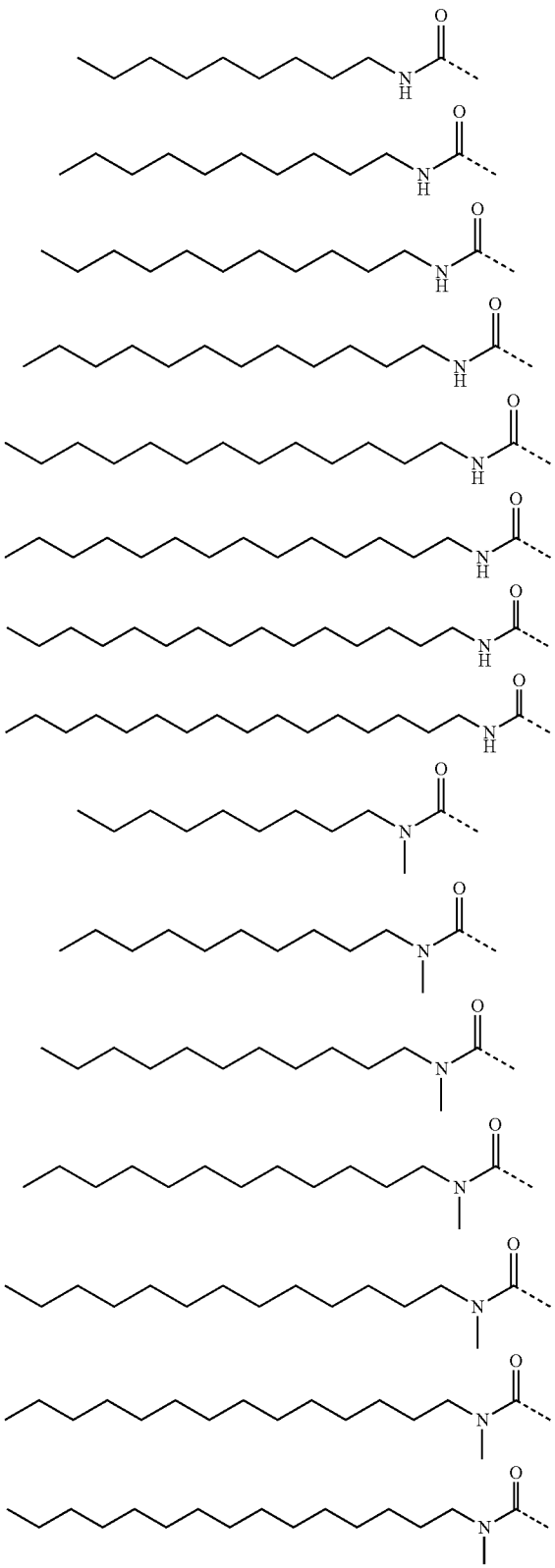

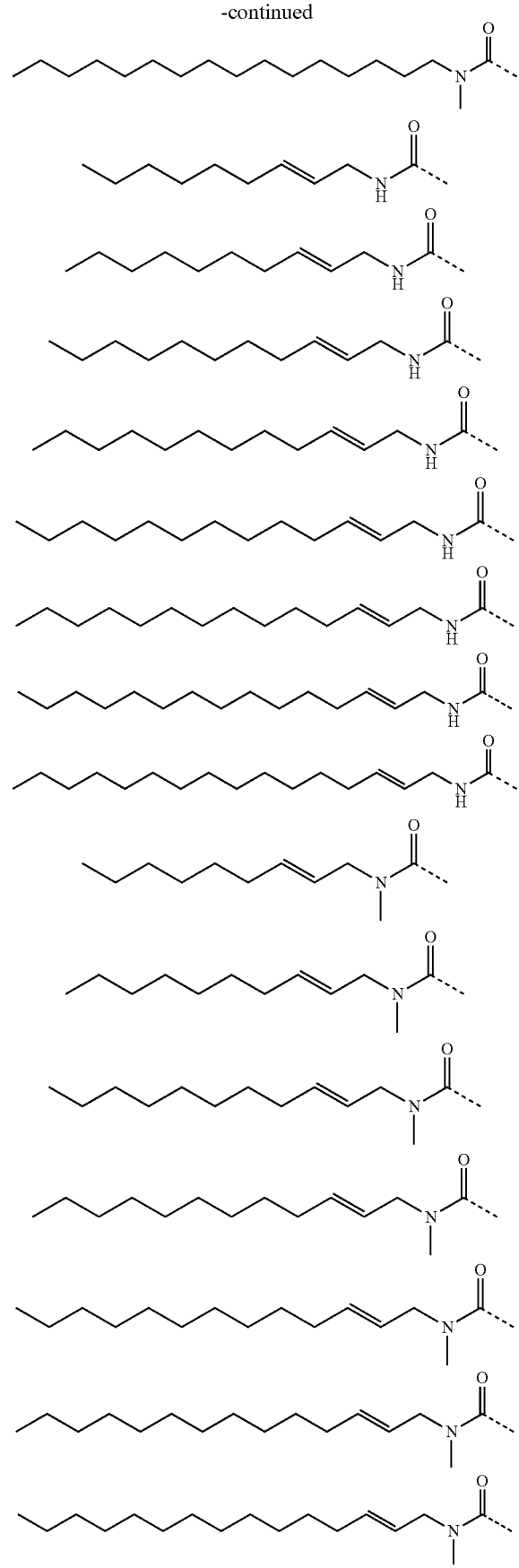
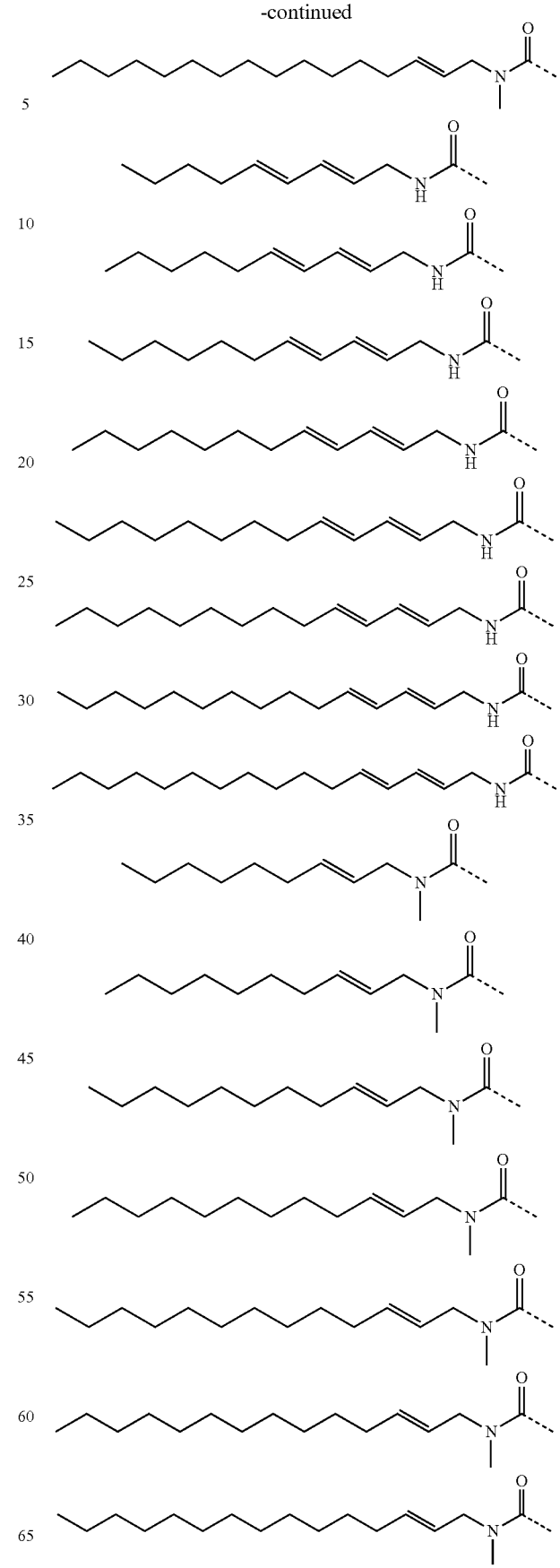

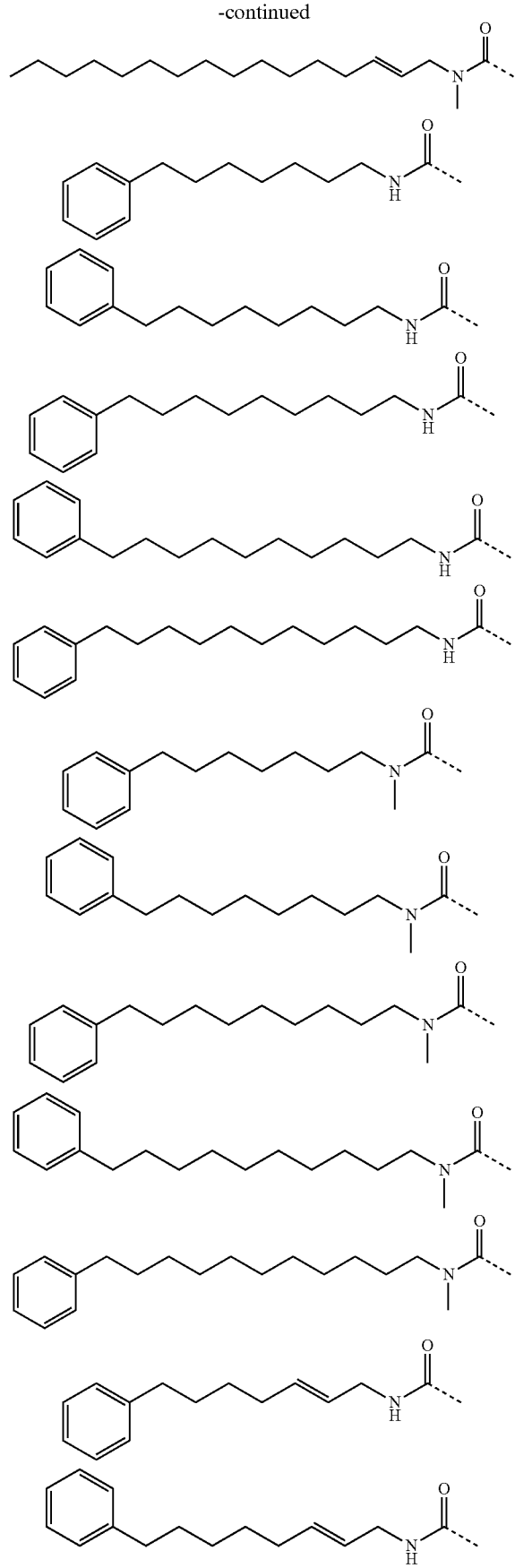
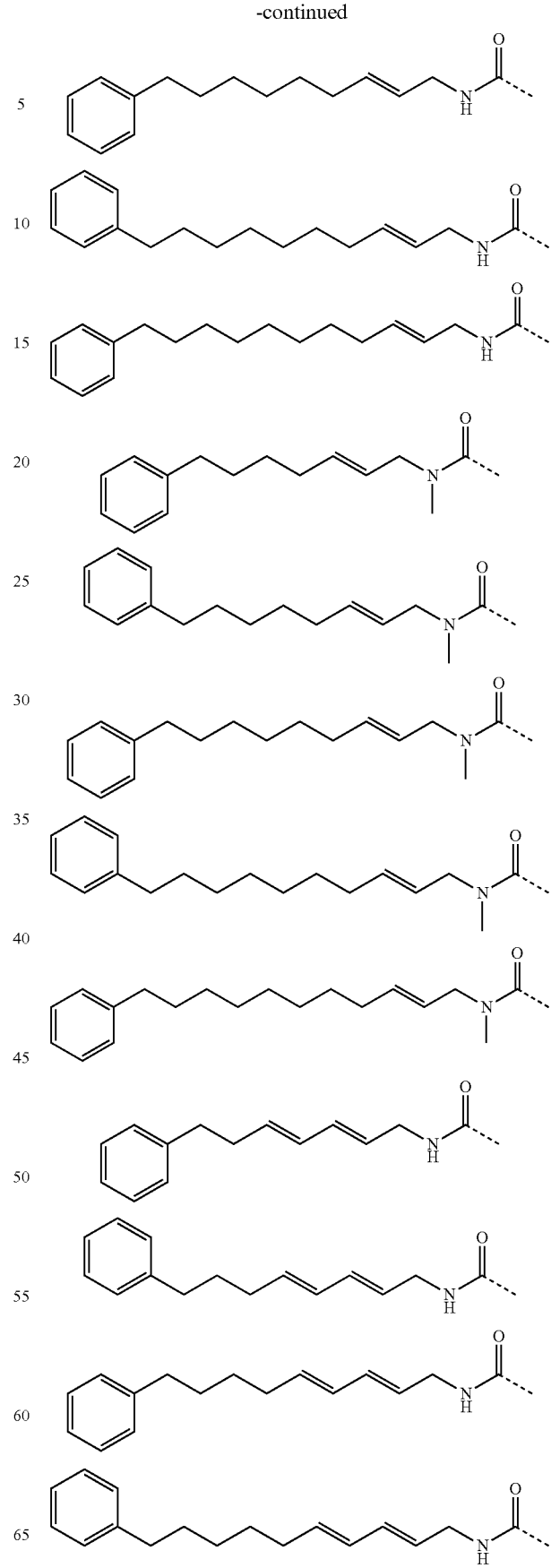

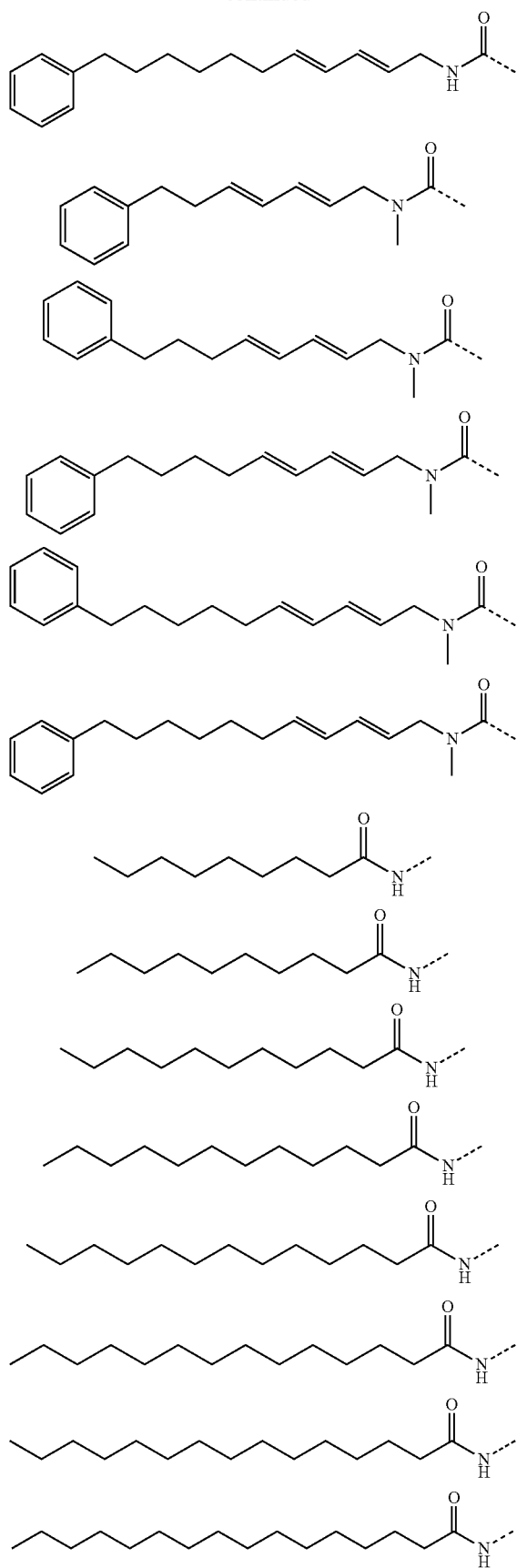

15
-continued
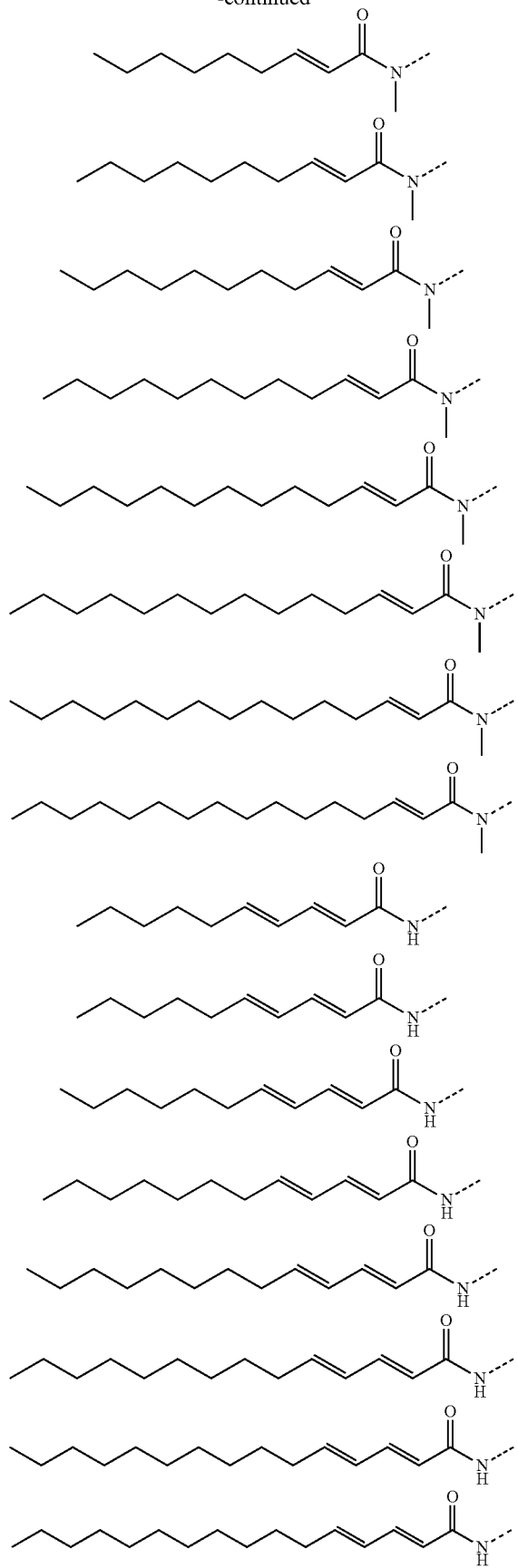
16
-continued
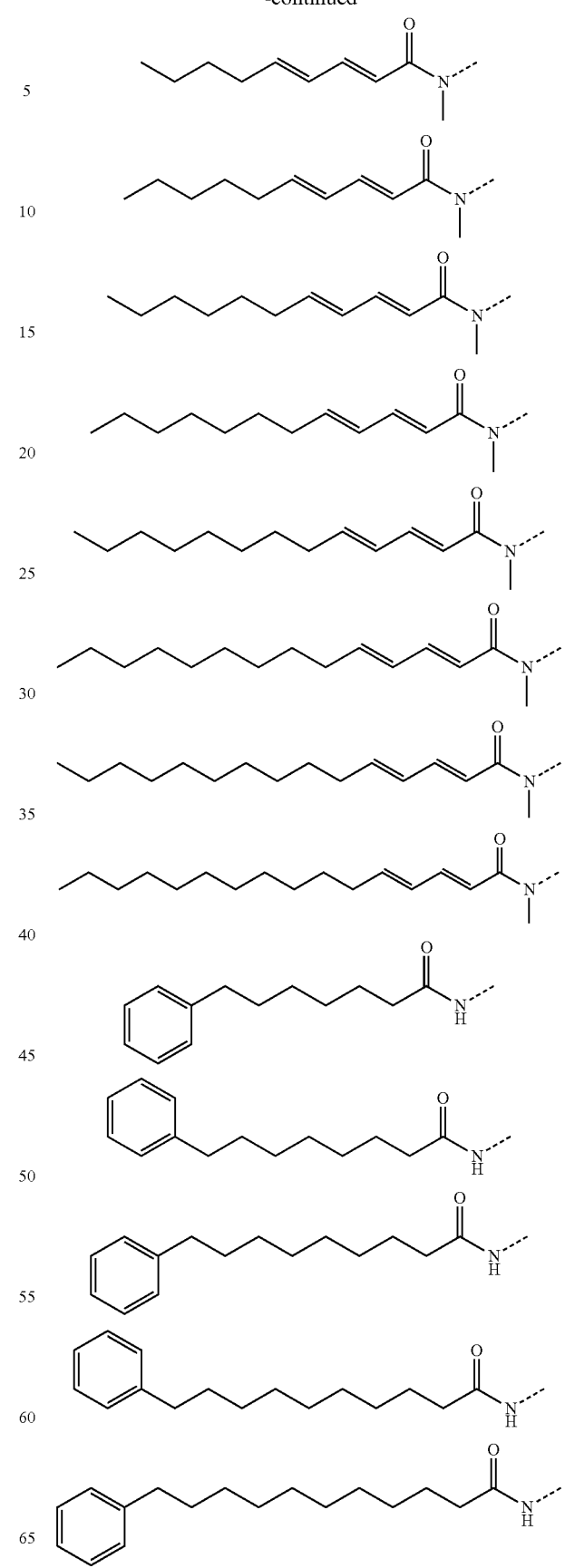

17
-continued
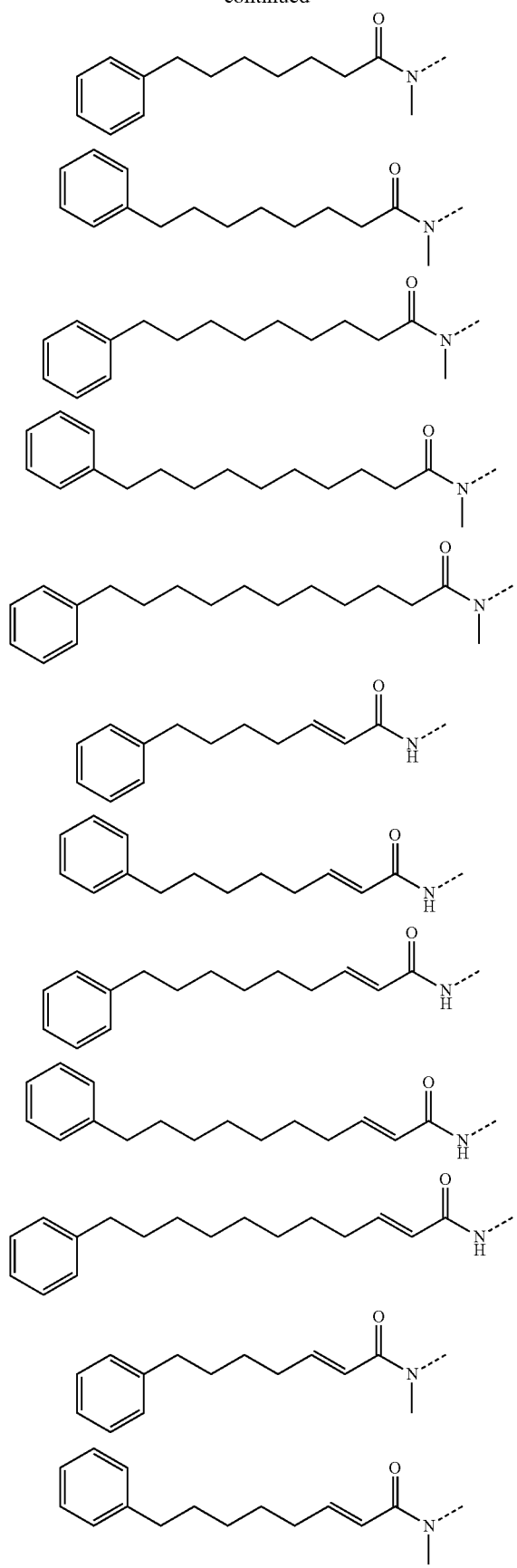
18
-continued
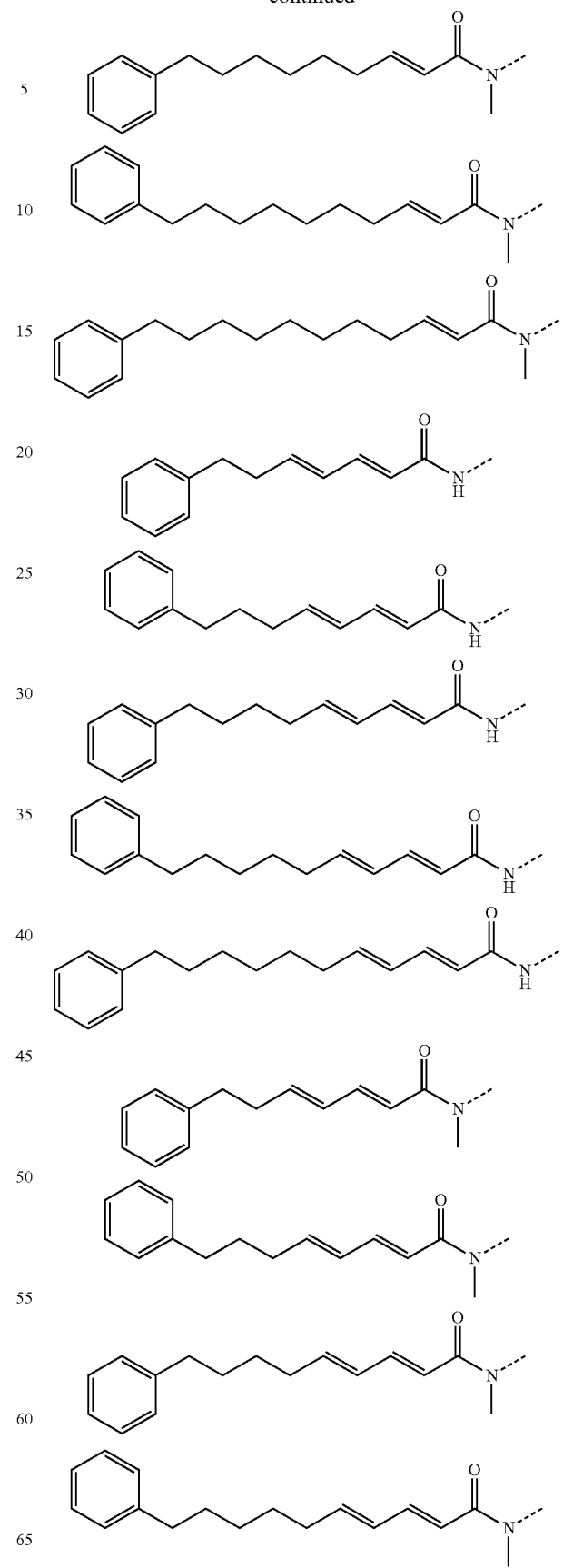

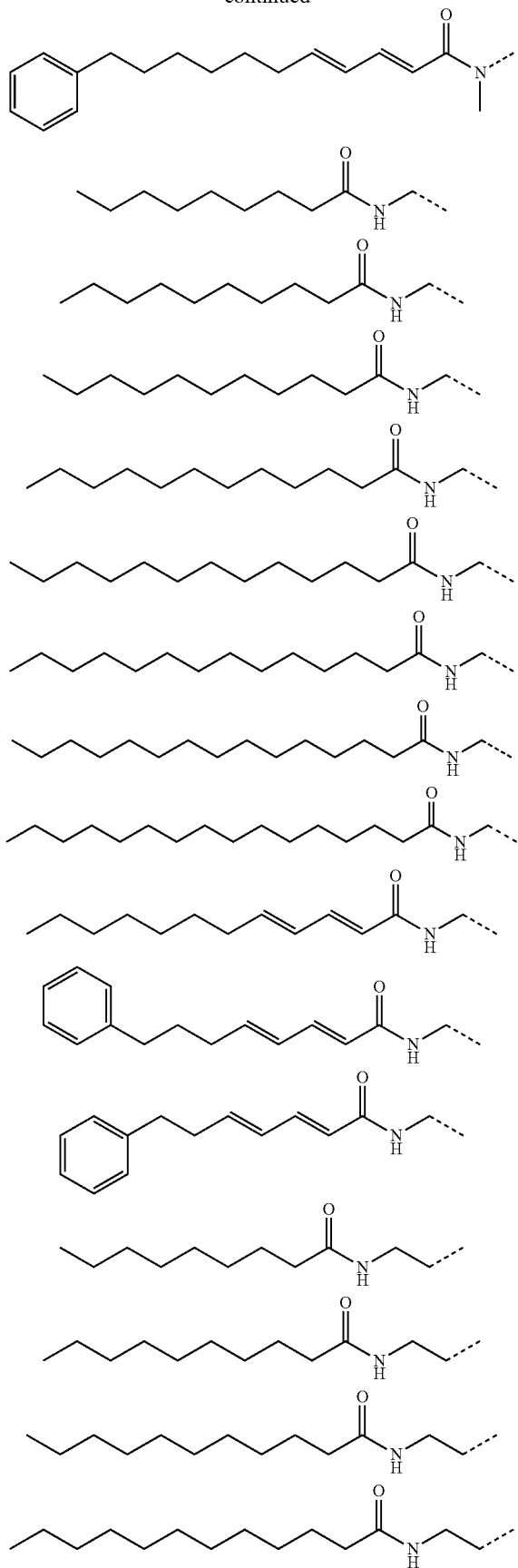
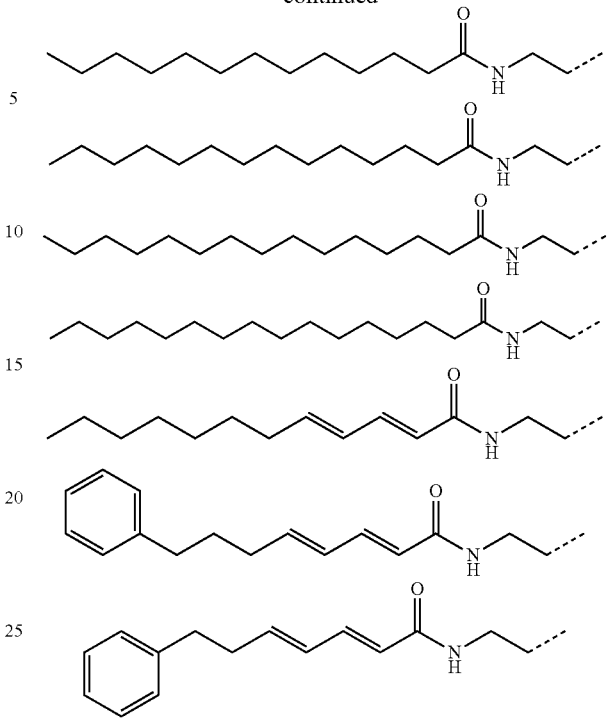

The compounds of structural formula (1) are effective as modulators of the endocannabinoid system and are particularly effective as inhibitors of AEAT (AEA transport) or FAAH. They are useful for the treatment and/or prevention of disorders responsive to inhibition of AEAT or FAAH, such as inflammation, irritation, itching, pruritus, pain, oedema and/or pro-allergic, allergic conditions and other diseases in particular with AEAT or FAAH involvement.

Optical Isomers-Diastereomers-Geometric Isomers-Tautomers

Compounds of structural formulae (1) and/or (2) contain one or more asymmetric centers and can occur as racemates and racemic mixtures, single enantiomers, diastereomeric mixtures and individual diastereomers. The present invention is meant to comprehend all such isomeric forms of the compounds of structural formulae (1) and/or (2).

Compounds of structural formulae (1) and/or (2) may be separated into their individual diastereomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formulae (1) and/or (2) may be obtained by stereospecific synthesis using optically pure starting materials or reagents of known absolute configuration.

Salts

The compounds according to the invention can be present in the form of pharmaceutical acceptable salts. The term "pharmaceutical acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, lithium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, parnoic, pantothenic, phosphoric, propionic, succinic, sulfuric, tartaric, p-toluenesulfonic, trifluoroacetic acid and the like. Particularly preferred are citric, fumaric, hydrobromic, hydrochloric, maleic, phosphoric, sulfuric and tartaric acids.

Administration, Dose Ranges and Formulation

The compounds of the invention are incorporated into pharmaceutical or cosmetic preparations by admixing them with a pharmaceutically or cosmetically acceptable carrier or excipient. Suitable carriers are known to the skilled person. Preferably the composition is a dermatological composition suitable to be applied topically on the skin or mucosa of a mammal. The form of the composition is not particularly limited, however, preferred forms are emulsions, suspensions and solutions. In certain embodiments, the compositions are in the form of lotions, creams, gels, solutions, sprays, cleansers, powders, ointments, waxes, lipsticks, soaps, shampoos, hydroalcoholic solutions, suspensions, foams, scrubs, saturated pads, skin or hair conditioning agents.

The compositions according to the invention, however, can be applied in any other way known to the skilled person such as oral or parenteral. Non-limiting examples are sublingual, vaginal, rectal, intravenous, nasal, intramuscular, inhalative, ocular and percutaneous. Suitable carriers and excipients are commonly known to the skilled person.

Compositions in accordance with the present invention may contain the 1,3-benzoxazol-2(3H)-one compounds in amounts of 0.001 to 40% by weight of the composition, preferably 0.01 to 5% by weight, more preferably 0.1 to 2% by weight and most preferably 0.5 to 1.5% by weight.

Compositions in accordance with the present invention may contain cosmetically and pharmaceutically/dermatologically acceptable auxiliaries usually employed in cosmetic and pharmaceutical preparations and known to the skilled person. These include for example preservatives, bactericides, perfumes, thickeners, emulsifiers, surfactants, softening agents, moisturizing agents, oils, fats, waxes, organic solvents, water, alcohols, polyols, polymers, foam stabilizers, anti-foaming agents, penetration enhancers or other conventional components of a pharmaceutical or cosmetic preparation.

Preparation of Compounds of the Invention

The compounds of formulae (1) and/or (2), when existing as a diastereomeric mixture, may be separated into diastereomeric pairs of enantiomers by fractional crystallization from a suitable solvent such as methanol, ethyl acetate or a mixture thereof. The pair of enantiomers thus obtained may be separated into individual stereoisomers by conventional means by using an optically active acid as a resolving agent. Alternatively, any enantiomer of a compound of the formulae (1) and/or (2) may be obtained by stereospecific syntheses using optically pure starting materials or reagents of known configuration.

The compounds of formulae (1) and/or (2) of the present invention can be prepared according to the procedures of the following schemes and examples, using appropriate materials and are further exemplified by the following specific examples. Moreover, by utilizing the procedures described herein, in conjunction with ordinary skill in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. Compounds containing a basic or acidic group can be further converted into the form of their pharmaceutical acceptable salts, such as described previously. All temperatures are degrees Celsius.

In the schemes, preparations and examples below, various reagent symbols and abbreviations have the following meanings:

AcOH acetic acid
Boc tert-butoxycarbonyl
Bu butyl
CDI 1,1'-carbonyldiimidazole
DBU 1,8-diazabicyclo[5.4.0]undec-7-ene
DCM dichloromethane
DIBAL-H diisobutylaluminum hydride
DIEA ethyl-diisopropylamine
DMAP 4-dimethylaminopyridine
DMF N,N-dimethylformamide
DMSO dimethyl sulfoxide
DPPA diphenyl phosphoryl azide
EDCI N-(3-dimethylaminopropyl)-N'-ethylcarbodiimide
Et ethyl
$Et_2O$ diethyl ether
EtOH ethanol
h hour(s)
HATU O-(7-azabenzotriazol-1-yl)-N,N,N',N"-tetramethyluronium hexafluorophosphate
HOAt 1-hydroxy-7-azabenzotriazole
m/z mass-to-charge ratio
Me methyl
min minute(s)
MeOH methanol
mp melting point
MW molecular weight
Ph phenyl
RT room temperature
TEA triethylamine
TEMPO 2,2,6,6-tetramethylpiperidine 1-oxyl
THF tetrahydrofuran
TLC thin layer chromatography
$t_R$ (min) HPLC retention time Reaction Scheme 1: Synthesis of ethyl (2E,4E)-2,4-dienoates and the corresponding acids using a Wittig-Horner reaction

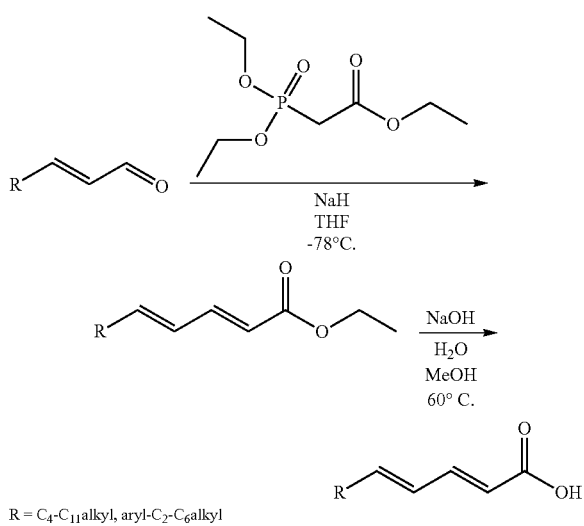

R = C$_4$-C$_{11}$alkyl, aryl-C$_2$-C$_6$alkyl

The starting material for the synthesis of compounds of the present invention, optionally substituted ethyl (2E,4E)-2,4-dienoates, can be obtained by reacting an optionally substituted (2E)-2-enal with a trialkylphosphonoacetate in the presence of a base such as sodium hydride or butyl lithium in an inert solvent like tetrahydrofuran at an appropriate temperature. Subsequent saponification with a base such as sodium hydroxide in a solvent like a mixture of water and methanol at a suitable temperature leads to the corresponding (2E,4E)-2,4-dienoic acid.

Reaction Scheme 2:
Alternative Synthesis of (2E,4E)-2,4-dienoic acids

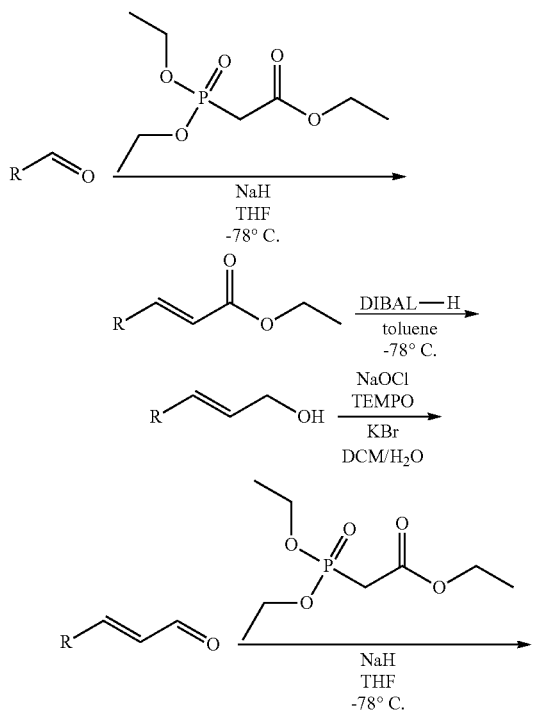

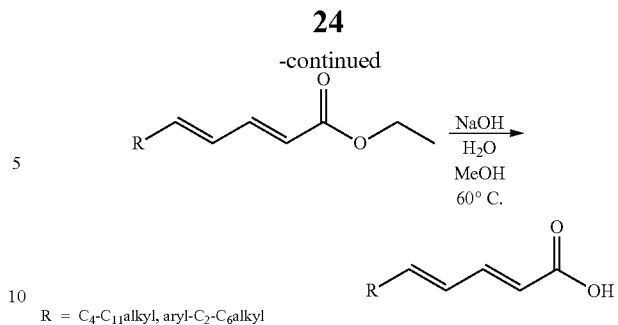

R = C$_4$-C$_{11}$alkyl, aryl-C$_2$-C$_6$alkyl

As shown in Reaction Scheme 2, the starting material for the synthesis of compounds of the present invention, optionally substituted ethyl (2E,4E)-2,4-dienoates and (2E,4E)-2,4-dienoic acids can also be prepared starting from optionally substituted saturated aldehydes. In this case the two double bonds with trans stereochemistry are introduced applying two Wittig-Horner reactions. α,β-Unsaturated ester is obtained by reaction of an aldehyde with trialkylphosphonoacetate in an inert solvent like tetrahydrofuran in the presence of a base such as sodium hydride or butyl lithium at low temperature. Reduction with DIBAL-H in a suitable solvent like toluene at −78° C. provides the corresponding allylic alcohol which is subsequently oxidized with sodium hypochlorite and TEMPO in the presence of potassium bromide in an appropriate solvent such as a mixture of water and dichloromethane to the α,β-unsaturated aldehyde. Alternatively, the alcohol can be oxidized applying a Swern oxidation using oxalyl chloride and DMSO in an appropriate solvent like DCM in the presence of a base such as triethylamine at −78° C. The aldehyde is subjected to a second Wittig-Horner reaction applying the conditions described above to yield the ethyl (2E,4E)-2,4-dienoate. Finally, (2E,4E)-2,4-dienoic acid is obtained by hydrolyzing the ester in the presence of a base such as aqueous sodium hydroxide in methanol at elevated temperature.

Reaction Scheme 3: Reduction of (2E,4E)-2,4-dienoic acid esters

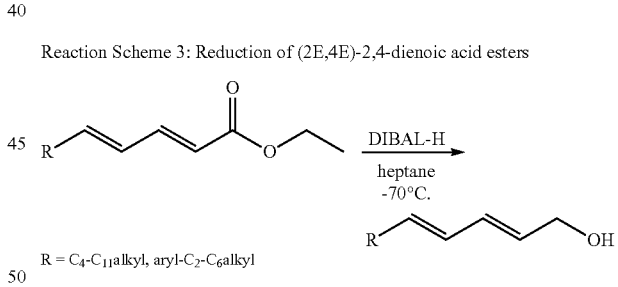

R = C$_4$-C$_{11}$alkyl, aryl-C$_2$-C$_6$alkyl

Optionally substituted (2E,4E)-2,4-dienoic acid ester can be reduced to the corresponding alcohol by reaction with a reducing reagent such as DIBAL-H in an inert solvent like heptane at a suitable temperature, as depicted in Reaction Scheme 3.

Reaction Scheme 4: Synthesis of (2E,4E)-2,4-dien-1-amines

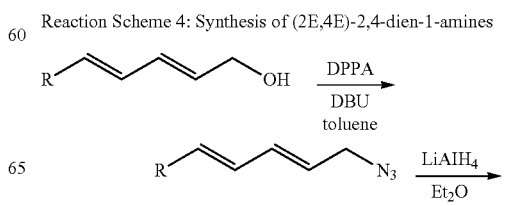

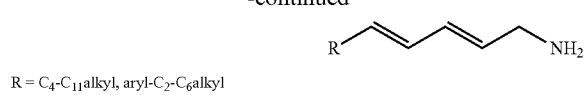

R = C$_4$-C$_{11}$alkyl, aryl-C$_2$-C$_6$alkyl

Reaction Scheme 4 shows the preparation of (2E,4E)-2,4-dien-1-amines. Optionally substituted (2E,4E)-2,4-dien-1-ylalcohol can be reacted with a reagent such as diphenyl phosphoryl azide in the presence of an appropriate base like 1,8-diazabicyclo[5.4.0]undec-7-ene in a solvent such as toluene to yield the corresponding azide. Subsequent reduction with a reducing agent like lithium aluminum hydride in an inert solvent such as diethyl ether at an appropriate temperature provides the target compound.

Alternatively, the azide can be reduced to the corresponding primary amine in a Staudinger reaction by reaction with triphenylphosphine in a suitable solvent such as a mixture of water and THF.

Reaction Scheme 5: Synthesis of (2E,4E)-N-alkyl-2,4-dien-1-amines

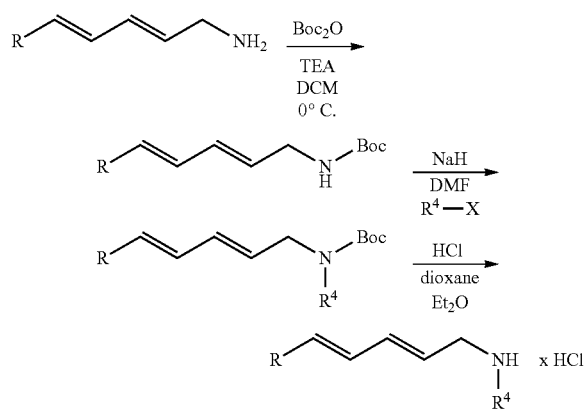

R = C$_4$-C$_{11}$alkyl, aryl-C$_2$-C$_6$alkyl

X = Cl, Br, I

Optionally substituted (2E,4E)-2,4-dien-1-ylamine can be converted to the corresponding N-alkylated amine as depicted in Reaction Scheme 5. Reaction with di-tert-butyl dicarbonate in the presence of a base like triethylamine in a suitable solvent like DCM is followed by an alkylation step with an alkyl halogenide like methyl iodide in a solvent like DMF in the presence of a base such as sodium hydride. The alkylated amine can be deprotected using a reagent like HCl in dioxane in an appropriate solvent like diethyl ether. The product can be isolated as hydrochloride salt or the free base can be liberated.

Reaction Scheme 6: Synthesis of amides

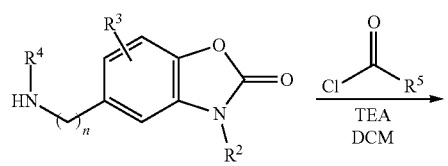

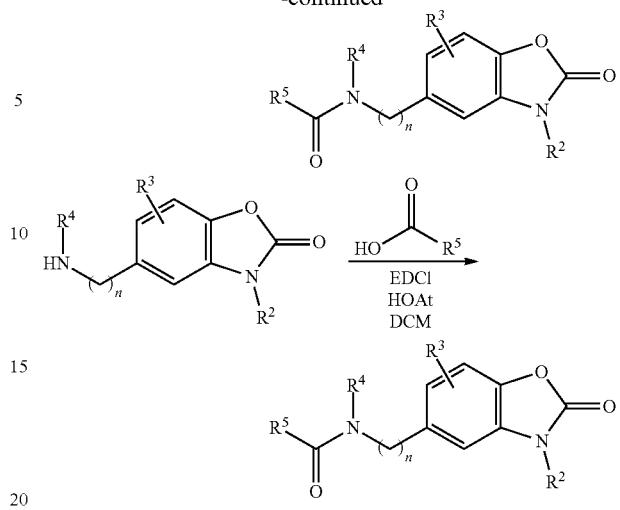

Acid chlorides from commercial sources can be used or optionally substituted carboxylic acid can be reacted with oxalyl chloride in an inert solvent such as DCM at an appropriate temperature to provide the corresponding acid chloride R$^5$COCl. Optionally substituted acid chloride can be reacted with optionally substituted 5-(omega-aminoalkyl)-1,3-benzoxazol-2(3H)-one in the presence of a base such as triethylamine in an inert solvent like dichloromethane to give access to the corresponding amide.

Alternatively, synthesis can also be accomplished by reacting the corresponding acid R$^5$COOH with optionally substituted 5-(omega-aminoalkyl)-1,3-benzoxazol-2(3H)-one in a solvent like DCM or DMF in the presence of a reagent such as HOAt and EDCI.

Reaction Scheme 7: Synthesis of 2-oxo-2,3-dihydro-1,3-benzoxazole-5-carboxamides

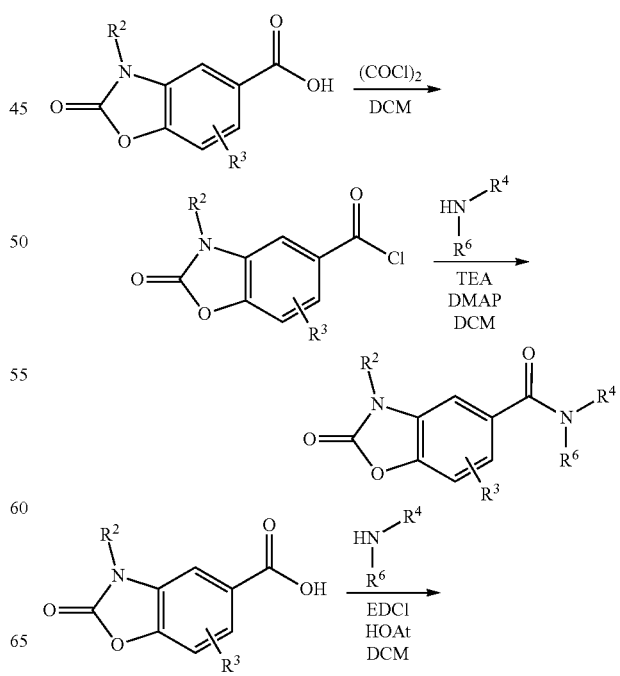

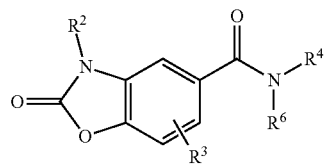

Optionally substituted 2-oxo-2,3-dihydro-1,3-benzoxazole-5-carboxylic acid can be converted to the corresponding acid chloride by reaction with a reagent such as oxalyl chloride or thionyl chloride in a suitable solvent like DCM. Reaction with an amine $HNR^4R^6$ in an inert solvent like DCM yields the desired product. The reaction can be carried out in the presence or without a base such as DMAP.

Alternatively, synthesis of optionally substituted 2-oxo-2,3-dihydro-1,3-benzoxazole-5-carboxylic acid amides can also be accomplished by reacting the corresponding acid with an amine $HNR^4R^6$ in a solvent like DCM or DMF in the presence of a reagent such as HOAt and EDCI.

Reaction Scheme 8:
Amide N-alkylation

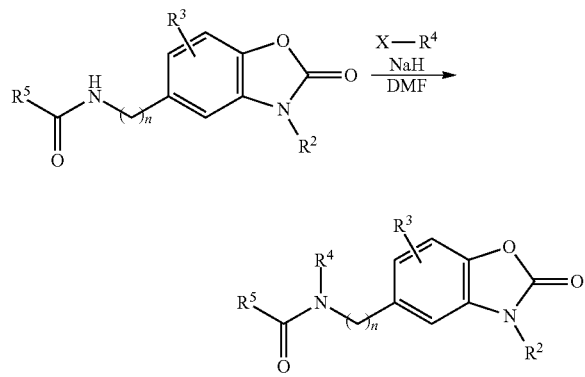

Substituents $R^4$ on the amide nitrogen atom can be introduced as show in Reaction scheme 8. The amide is deprotonated with a suitable base such as sodium hydride in an appropriate solvent like DMF and subsequently reacted with a reagent $X—R^4$ in which X represents a leaving group such as a halogenide.

Reaction Scheme 9: Synthesis of substituted 5-amino-1,3-benzoxazol-2(3H)-ones

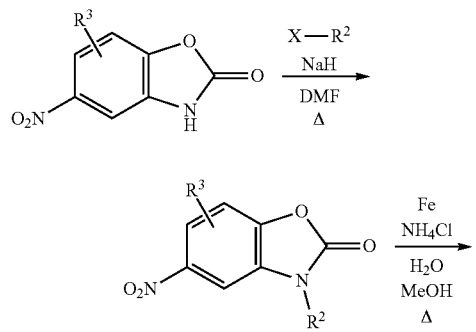

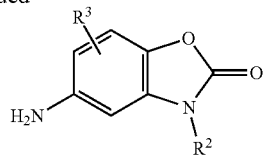

Substituted 5-amino-1,3-benzoxazol-2(3H)-ones can be obtained as depicted in Reaction scheme 9. Optionally $R^3$-substituted 5-nitro-1,3-benzoxazol-2(3H)-ones are deprotonated with a suitable base such as sodium hydride in an appropriate solvent like DMF at elevated temperature and subsequently reacted with a reagent $X—R^2$ in which X represents a leaving group such as a halogenide. The nitro group can for example be reduced applying reagents like iron and ammonium chloride in a mixture of water and methanol at elevated temperature to yield the target compounds.

Analytical LC-MS
Analytical Conditions Summary:

Agilent 1100 with ELSD (PL-ELS 2100) and diode array detector with UV-detection between 220 and 320 nm and Mass Selective Detector (MSD) in ESI+ and ESI− modus (mass range: m/z=100-800),
Column: Waters Xbridge C18, 3.5 μm, 2.1 mm×50 mm;
Flow rate of 0.8 ml/min; column temperature: 30° C.;
Mobile Phase A: acetonitrile (0.1% HCOOH)
Mobile Phase B: water (0.1% HCOOH)

or

Agilent 1200 with diode array detector with UV-detection between 220 and 320 nm and Mass Selective Detector (MSD) in ESI+ and ESI− modus (mass range: m/z=100-800),
Column: Waters Xbridge C18, 3.5 μm, 2.1 mm×50 mm;
Flow rate of 0.8 ml/min; column temperature: 30° C.;
Mobile Phase A: acetonitrile (0.1% HCOOH)
Mobile Phase B: water (0.1% HCOOH)
Gradient A:
linear gradient from 2% to 98% acetonitrile in water (0.1% HCOOH)

| 0.0 min | 2% A |
| 3.5 min | 98% A |
| 6.0 min | 98% A |

Agilent 1100 with ELSD (PL-ELS 2100) and diode array detector (Agilent G1315B) with UV-detection between 220 and 320 nm and Mass Selective Detector (MSD, Agilent LC/MSD G6130B) in ESI+ and ESI− modus (mass range: m/z=100-800),
Column: Waters Xbridge C18, 3.5 μm, 2.1 mm×50 mm;
Flow rate of 0.8 ml/min; column temperature: 30° C.;
Mobile Phase A: 95% acetonitrile+5% 10 mM ammonium bicarbonate in water
Mobile Phase B: 10 mM ammonium bicarbonate in water (pH=9.5)
Gradient B:
linear gradient from 2% to 98% of 95% acetonitrile+5% 10 mM ammonium bicarbonate in water

| 0.0 min | 2% A |
| 3.5 min | 98% A |
| 6.0 min | 98% A |

Column: Waters Xselect C18, 3.5 μm, 2.1 mm×50 mm;
Flow rate of 0.8 ml/min; column temperature: 25° C.;
Mobile Phase A: 95% acetonitrile+5% 10 mM ammonium bicarbonate in water
Mobile Phase B: 10 mM ammonium bicarbonate in water (pH=9.5)

Gradient C:
Agilent 1100 with ELSD (PL-ELS 2100) and diode array detector with UV-detection between 220 and 320 nm and Mass Selective Detector (MSD) in ESI+ and ESI− modus (mass range: m/z=100-800),
Column: Waters Xselect C18, 3.5 μm, 2.1 mm×50 mm;
Flow rate of 0.8 ml/min; column temperature: 35° C.;
Mobile Phase A: acetonitrile (0.1% HCOOH)
Mobile Phase B: water (0.1% HCOOH)
linear gradient from 2% to 98% acetonitrile in water (0.1% HCOOH)

| 0.0 min | 2% A |
| 3.5 min | 98% A |
| 8.0 min | 98% A |

Gradient D:
Agilent 1100 with ELSD (PL-ELS 2100) and diode array detector with UV-detection between 220 and 320 nm and Mass Selective Detector (MSD) in ESI+ and ESI− modus (mass range: m/z=100-800),
Flow rate of 0.8 ml/min; column temperature: 35° C.;
Mobile Phase A: 95% acetonitrile+5% 10 mM ammonium bicarbonate in water
Mobile Phase B: 10 mM ammonium bicarbonate in water (pH=9.5)
linear gradient from 2% to 98% acetonitrile in water (0.1% HCOOH)

| 0.0 min | 2% A |
| 3.5 min | 98% A |
| 8.0 min | 98% A |

The following describes the detailed examples of the invention which have been prepared via reaction schemes 1 to 9.

TABLE 1

| No. | R² | R¹ | HPLC $t_R$ (min) | HPLC method | MS MW (calc.) free base | MS [M + H⁺] (found) |
|---|---|---|---|---|---|---|
| 1 | H | (C11 alkyl amide) | 4.25 | B | 332.45 | 333 |
| 2 | Me | (C11 alkyl amide) | 4.50 | B | 346.47 | 347 |
| 3 | H | (C13 alkyl amide) | 4.25 | A | 346.47 | 347 |
| 4 | H | (dienyl amide) | 4.08 | A | 342.44 | 343 |
| 5 | Me | (C13 alkyl amide) | 4.41 | A | 360.50 | 361 |
| 6 | Me | (dienyl amide) | 4.30 | B | 356.47 | 357 |
| 7 | Me | (dienyl amide) | 4.25 | B | 342.44 | 343 |

TABLE 1-continued
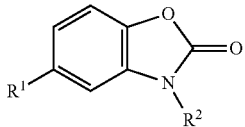
| No. | R² | R¹ | HPLC tR (min) | method | MS MW (calc.) free base | [M + H⁺] (found) |
|---|---|---|---|---|---|---|
| 8 | H | 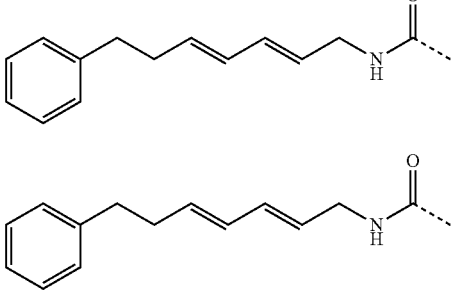 | 3.56 | A | 348.41 | 349 |
| 9 | Me | 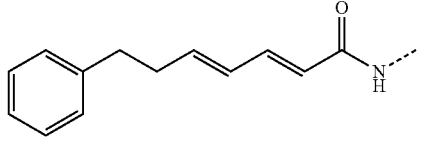 | 3.69 | A | 362.43 | 363 |
| 10 | Me | 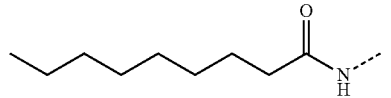 | 3.79 | B | 348.41 | 349 |
| 11 | Me | 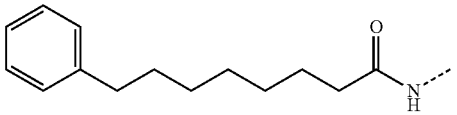 | 3.75 | A | 304.39 | 305 |
| 12 | Me | 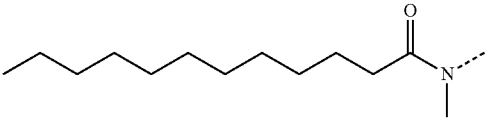 | 3.87 | A | 366.46 | 367 |
| 13 | Me | 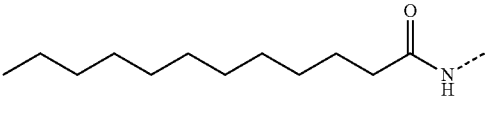 | 4.32 | C | 360.50 | 361 |
| 14 | —(CH₂)₂OH | 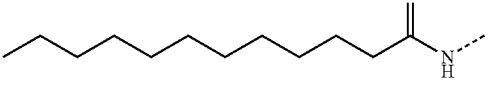 | 4.06 | C | 376.50 | 377 |
| 15 | Et | 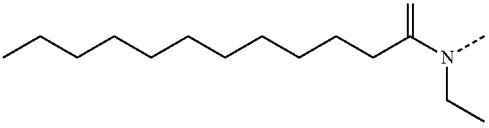 | 4.64 | D | 360.50 | 361 |
| 16 | Me | 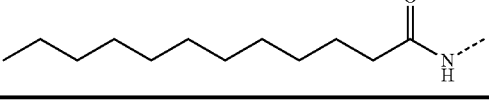 | 4.32 | C | 374.53 | 375 |
| 17 | Bu |  | 4.71 | C | 388.55 | 389 |

The following examples are provided to illustrate the invention and are not limiting the scope of the invention in any manner.

Common Intermediates

Ethyl (2E,4E)-dodeca-2,4-dienoate

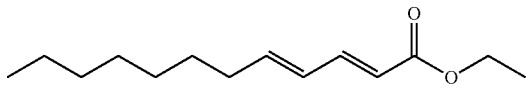 [SMILES: CCCCCCC/C=C/C=C/C(=O)OCC]

Sodium hydride (60% wt., 3.11 g) was suspended in dry tetrahydrofuran (200 ml) and cooled to 0° C. O,O-Diethyl ethoxycarbonylmethyl phosphonate (15.43 ml) was added dropwise. The reaction mixture was stirred at 0° C. for 30 min and cooled to −78° C. after which (E)-dec-2-enal (11.90 ml) was added dropwise. Stirring was continued at this temperature for 2 h, after which the mixture was warmed to room temperature. The reaction mixture was poured into water, and the aqueous phase was extracted with ethyl acetate. The combined organic layer was washed with brine, dried over sodium sulfate, and the solvent was evaporated. The crude product was purified by column chromatography.

(2E,4E)-dodeca-2,4-dienoic acid

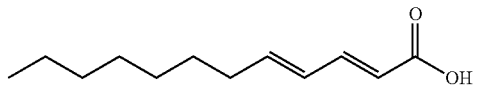

Ethyl (2E,4E)-dodeca-2,4-dienoate (11.84 g) was dissolved in methanol (130 ml) and 2M aqueous sodium hydroxide solution (35 ml) was added. The reaction mixture was heated to 60° C. until full conversion was observed. After cooling down to room temperature the mixture was acidified with diluted aqueous HCl. The reaction mixture was extracted with ethyl acetate and the organic layer was washed with brine, dried over sodium sulfate, and solvents were evaporated. The crude product was used for the next step without further purification.

(2E,4E)-dodeca-2,4-dienoyl chloride

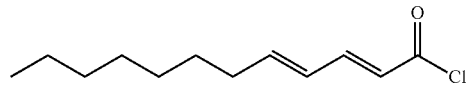

(2E,4E)-dodeca-2,4-dienoic acid (2.5 g) was dissolved in dichloromethane (25 ml). Oxalyl chloride (2.23 ml) was added and the reaction mixture was stirred at room temperature for 3 h. Solvent and excess oxalyl chloride were removed, and the residue was stripped several times with DCM. The crude acid chloride was used as such in next step.

(2E,4E)-Dodeca-2,4-dien-1-ol

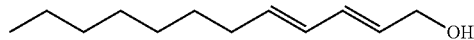

Under nitrogen atmosphere, (2E,4E)-ethyl dodeca-2,4-dienoate (6.1 g) was dissolved in n-heptane (120 ml) and cooled to −70° C. DIBAL-H in hexanes (82 ml) was added dropwise and the mixture was stirred at −70° C. for 45 min. Brine (60 ml) and diethyl ether (100 ml) were added and the mixture was stirred for 45 min while warming to RT. The organic layer was separated and washed with 1N HCl, dried over sodium sulfate, filtered and concentrated. A colorless liquid was isolated that solidified upon slight cooling.

(2E,4E)-1-Azidodeca-2,4-diene

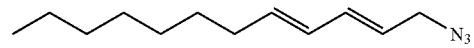

(2E,4E)-Dodeca-2,4-dien-1-ol (4.95 g) was dissolved in dry toluene (110 ml) and diphenylphosphinyl azide (7.92 g) was added. DBU (4.91 ml) was added dropwise. The mixture turned opaque under evolution of heat. The solvent was evaporated and diethyl ether was added to the residue. The reaction mixture was washed with 1M HCl, 1M NaOH and brine and the organic layer was dried over sodium sulfate, filtered and concentrated to give a light yellow liquid. The crude product was filtered over silica gel.

(2E,4E)-Dodeca-2,4-dien-1-amine

Under nitrogen atmosphere, 1 M LiAlH$_4$ in diethyl ether (2.89 ml) was diluted with dry diethyl ether (30 ml) and cooled in an ice bath. A solution of (2E,4E)-1-azidododeca-2,4-diene (1 g) in dry diethyl ether (10 ml) was added slowly. The mixture was stirred at 0° C. for 1 h, the ice bath was removed and stirring was continued for 1 h while warming to room temperature. Water was added carefully until gas evolution ceased and the reaction mixture was dried over sodium sulfate, filtered and concentrated to give a yellow liquid.

Ethyl (2E)-5-phenylpent-2-enoate

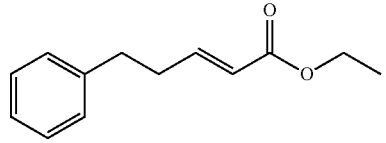

Sodium hydride (60% wt., 181 mg) was suspended in dry tetrahydrofuran (5 ml) and cooled to 0° C. Triethyl phosphonoacetate (896 μl) was added dropwise. The reaction mixture was stirred at 0° C. for 30 min. After cooling to −78° C. 3-phenylpropionaldehyde (500 μl) was added dropwise. The reaction mixture was stirred at this temperature for 1 h. The reaction mixture was allowed to warm-up to room temperature, hydrolyzed with water/THF, poured into water and the aqueous layer was extracted twice with EtOAc. The combined organic layer was washed with brine, dried over Na$_2$SO$_4$, and concentrated. The crude was purified by flash column chromatography.

(2E)-5-Phenylpent-2-enal

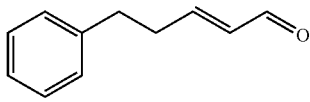 [SMILES: O=C/C=C/CCc1ccccc1]

A solution of (E)-ethyl 5-phenylpent-2-enoate (732 mg) in dry toluene (5 ml) was cooled to −78° C. DIBAL-H (1 M in hexanes, 7.17 ml) was added dropwise and the mixture was stirred for 3 h. A second portion of DIBAL-H (1 M in hexanes, 0.717 ml) was added and stirring was continued for another 3 h. The mixture was allowed to warm-up to RT and hydrolyzed with 1 M aqueous HCl (5 ml). Additional 3M aqueous HCl was added until pH=1 and the aqueous layer was extracted with EtOAc (3×). The combined organic layer was washed with brine, dried over Na$_2$SO$_4$ and concentrated. The crude product was dissolved in dichloromethane (5 ml) and TEMPO (28.0 mg), potassium bromide (42.6 mg) and water (5 ml) were added. Aqueous sodium hypochlorite solution (13%, 1.642 ml) was added dropwise. The mixture was stirred at room temperature for 15 h. After phase separation the aqueous layer was extracted with CH$_2$Cl$_2$. The combined organic layer was washed with 1 M HCl, water and brine, dried over Na$_2$SO$_4$ and concentrated. The crude product was purified by flash column chromatography to yield a slightly orange oil.

Ethyl (2E,4E)-7-phenylhepta-2,4-dienoate

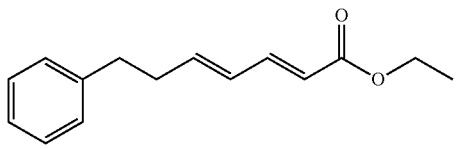 [SMILES: CCOC(=O)/C=C/C=C/CCc1ccccc1]

Sodium hydride (60% wt., 74.0 mg) was suspended in dry tetrahydrofuran (5 ml) and cooled to 0° C. Triethyl phosphonoacetate (0.367 ml) was added dropwise. The reaction mixture was stirred at 0° C. for 30 min and subsequently cooled to −78° C. after which (E)-5-phenylpent-2-enal (247 mg) was added dropwise. The reaction mixture was stirred at this temperature for 1 h. The cooling bath was removed and the reaction mixture was stirred for an additional hour. The reaction mixture was hydrolyzed with water/THF, poured into water and the aqueous layer was extracted with twice with EtOAc. The combined organic layer was washed with brine, dried over Na$_2$SO$_4$, and concentrated. The crude product was used as such in next step.

(2E,4E)-7-Phenylhepta-2,4-dienoic acid

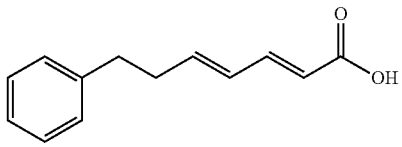 [SMILES: O=C(O)/C=C/C=C/CCc1ccccc1]

(2E,4E)-Ethyl 7-phenylhepta-2,4-dienoate (355 mg) was dissolved in methanol (5 ml). 2M aqueous sodium hydroxide (1.002 ml) was added and the resulting suspension was heated to 60° C. The reaction mixture was stirred for 2 h. After cooling to room temperature the mixture was acidified with 1M aqueous HCl and extracted three times with EtOAc. The combined organic layer was washed with brine, dried over Na$_2$SO$_4$ and concentrated to yield an off-white solid. The residue was taken up with 1M aqueous NaOH (10 ml) and extracted with Et$_2$O. The aqueous layer was acidified with 2M aqueous HCl and extracted twice with EtOAc. The combined EtOAc layer was washed with brine, dried over Na$_2$SO$_4$ and concentrated.

(2E,4E)-7-Phenylhepta-2,4-dien-1-ol

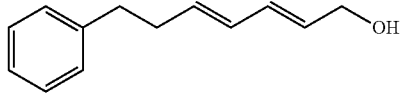 [SMILES: OC/C=C/C=C/CCc1ccccc1]

A solution of ethyl (2E,4E)-7-phenylhepta-2,4-dienoate (7.32 g) in dry toluene (75 ml) was cooled to −78° C. DIBAL-H (1M in hexanes, 65.2 ml) was added dropwise and the mixture was stirred for 3 h. The mixture was allowed to warm-up to room temperature and hydrolyzed with 1M aqueous HCl with cooling in ice/water bath. Additional, 3M aqueous HCl was added until pH=1. The layers were separated and the aqueous layer was extracted three times with EtOAc. The combined organic layer was washed with brine, dried over Na$_2$SO$_4$ and concentrated. The crude product was purified by column chromatography to yield a colorless oil.

[(3E,5E)-7-azidohepta-3,5-dien-1-yl]benzene

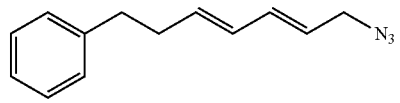 [SMILES: [N-]=[N+]=NC/C=C/C=C/CCc1ccccc1]

(2E,4E)-7-Phenylhepta-2,4-dien-1-ol (6.8 g) was dissolved in dry toluene (130 ml) and cooled in an ice-salt bath. Diphenyl phosphorazidate (7.83 ml) was added, followed by dropwise addition of DBU (6.53 ml) in dry toluene (15 ml). The mixture was stirred for 15 h while warming to room temperature. Solvents were evaporated and the residue was partitioned between diethyl ether and 1N NaOH. The organic layer was washed with brine, dried over sodium sulfate, filtert-Butyl
[(2E,4E)-7-phenylhepta-2,4-dien-1-yl]carbamate

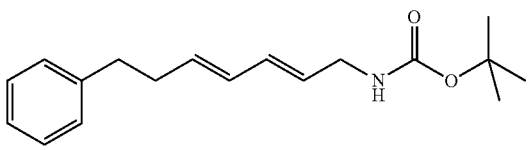 [SMILES: CC(C)(C)OC(=O)NC/C=C/C=C/CCc1ccccc1]

Under a nitrogen atmosphere, LiAlH₄ (4N in diethyl ether, 4.50 ml) and dry diethyl ether (200 ml) were cooled to 0° C. A solution of [(3E,5E)-7-azidohepta-3,5-dien-1-yl]benzene (6.4 g) in dry diethyl ether (70 ml) was added dropwise and the mixture was stirred at 0° C. for 1 h, then at room temperature for 1 h. Water was added dropwise until gas evolution ceased. The mixture was dried over sodium sulfate, filtered and concentrated to give intermediate amine as a yellow liquid. Intermediate amine (5.6 g) was dissolved in dichloromethane (150 ml) and cooled to 0° C. Triethylamine (4.60 ml) was added, followed by Boc₂O (6.97 ml). The cooling bath was removed and the mixture was stirred at room temperature for 15 h. Water (200 ml) was added and the organic layer was separated. The aqueous layer was extracted with dichloromethane (200 ml). The combined organic layer were dried over sodium sulfate, filtered and concentrated. The crude product was purified by column chromatography to yield a colourless liquid.

(2E,4E)-7-Phenylhepta-2,4-dien-1-amine

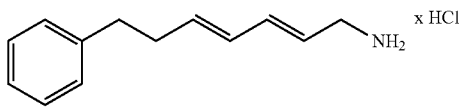 [SMILES: NC/C=C/C=C/CCc1ccccc1]

tert-Butyl (2E,4E)-7-phenylhepta-2,4-dienylcarbamate (800 mg) was dissolved in hydrochloric acid in dioxane (4.0M, 8.35 ml). The mixture was stirred at room temperature for 1 h. The solvent was evaporated and co-evaporated twice with Et₂O, Et₂O was added, the solids were filtered off under a stream of nitrogen to yield the product as an off white solid.

Synthesis of Example 4

Example 4

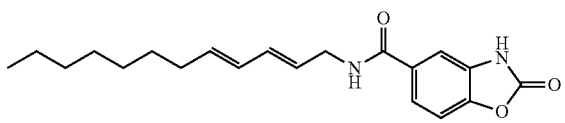 [SMILES: CCCCCCC/C=C/C=C/CNC(=O)c1ccc2oc(=O)[nH]c2c1]

To a cooled (0° C.) solution of 2-oxo-2,3-dihydrobenzo[d]oxazole-5-carboxylic acid (150 mg) and (2E,4E)-dodeca-2,4-dien-1-amine (138 mg) in dichloromethane (3 ml) and dry N,N-dimethylformamide (2 ml) was added EDCI.HCl (161 mg) followed by 1-hydroxy-7-azabenzotriazole (10.36 mg) and the reaction mixture was stirred at room temperature overnight. The reaction mixture was concentrated under reduced pressure. The crude material was dissolved in EtOAc and eluted over a small silica pad using EtOAc followed by evaporation under reduced pressure to afford a crude yellow solid. To the crude solid was added H₂O and EtOAc, the mixture was heated while vigorously stirring until complete dissolution occurred. After separation of the layers while still hot, the organic EtOAc layer was filtered using a phase separator and evaporated to dryness under reduced pressure. Further purification via reversed phase column chromatography gave the product as a white solid.

Synthesis of Example 10

Example 10

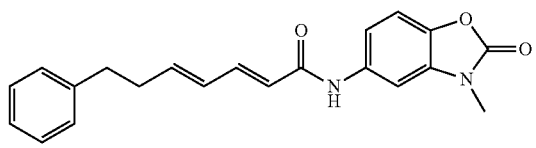 [SMILES: Cn1c(=O)oc2ccc(NC(=O)/C=C/C=C/CCc3ccccc3)cc21]

To a suspension of 5-amino-3-methyl-1,3-benzoxazol-2(3H)-one (125 mg) and (2E,4E)-7-phenylhepta-2,4-dienoic acid (140 mg) in dichloromethane (3 ml) and dry N,N-dimethylformamide (2 ml) was added EDCI.HCl (146 mg) followed by 1-hydroxy-7-azabenzotriazole (9.42 mg) and the reaction mixture was stirred at room temperature overnight. The mixture was concentrated and purified by flash column chromatography (10-70% EtOAc in heptane) to yield the product as a white solid.

Examples 1-3, 5-9 and 11-17 as indicated in Table 1 above have been prepared in an analogues manner as Examples 4 and 10 using the respective starting compounds.

Biological Assays

A. Radioligand Displacement Assays on CB₁ and CB₂ Receptors

For the CB₁ receptor, binding experiments were performed in the presence of 0.5 nM of the radioligand [³H]CP55,940 (168 Ci/mmol) (Perkin Elmer, Waltham, Mass., US) at 30° C. in siliconized glass vials together with 8.0 μg of membrane recombinantly over-expressing CB₁ (No. RBHCB1M, Perkin Elmer, Waltham, Mass., US), which was resuspended in 0.5 ml (final volume) assay-buffer (50 mM TRIS-HCl, 2.5 mM EDTA, 5 mM MgCl₂, 0.5 mg/ml fatty acid free BSA, pH 7.4). Test compounds were present at varying concentrations and the non-specific binding of the radioligand was determined in the presence of 10 μM WIN55, 212-2 (Tocris Cookson Ltd., Bristol, UK). After 2 h incubation, the suspension was rapidly filtered through 0.1% polyethylenimine pre-soaked UniFilter®-96 GF/B (Perkin Elmer, Boston Mass., US) washed twelve times with 167 μl ice-cold assay-buffer. Radioactivity on dried and sealed filter plates was measured with a Perkin Elmer 1450 Microbeta TRILUX liquid scintillation counter in 40 μl MicroScint 20 scintillation cocktail (Perkin Elmer, Waltham, Mass., US). Data collected from three independent experiments performed in triplicates were normalized between 100% and 0% specific binding for [³H]CP55,940. These data were graphically linearized by projecting Hill-plots, which allowed the calculation of IC₅₀ values. Derived from the dissociation constant (K_D) of [³H]CP55,940 and the concentration-dependent displacement (IC₅₀ value), inhibition constants ($K_i$) of competitor compounds were calculated using the Cheng-Prusoff equation [$K_i=IC_{50}/(1+L/K_D)$].

For $CB_2$-receptor binding studies 3.8 μg of membrane recombinantly over-expressing $CB_2$ (No. RBXCB2M, Perkin Elmer, Waltham, Mass., US) were resuspended in 0.5 ml assay buffer (see above) together with 0.5 nM of the radioligand [$^3$H]CP55,940. The $CB_2$-binding assay was conducted in the same manner as for $CB_1$.

B. Critical micelle concentration (CMC) measurements

Dye micellization was carried out with a modified version of the method described by Eliyahu et al., *Novel dextran-spermine conjugates as transfecting agents: comparing water-soluble and micellar polymers*. Gene Ther. 2005 March; 12(6):494-503. Compounds (from 2 mM stock solutions) were mixed at increasing concentrations with 0.1 nM fluorescein (free acid, 99%, Fluka, Switzerland) at room temperature in Nanopure distilled water. Experiments were carried out on 96-well microtiter plates (excitation at 485 nm, emission at 535 nm). Since the emission of fluorescein is pH-dependent, the pH of the mixture was kept constant at 6.9. The CMC range was determined as the concentration range where the first statistically significant increase in fluorescence was detected. At an appropriate resolution of the concentration range this increase was not gradual but sudden.

C. Cellular Uptake of [$^3$H]-AEA

Human lymphoma U937 cells were grown in RPMI 1640 medium (Invitrogen, Basel, Switzerland) supplemented with 10% fetal bovine serum, 1 g/ml fungizone (amphotericin B), 100 units/ml penicillin, 100 g/ml streptomycin, and 2 mM L-glutamine (all from Invitrogen) and selected for the cellular AEA uptake assay. $2.5 \times 10^6$ cells were collected and suspended in 250 μl of RPMI 1640 medium (Invitrogen, Basel, Switzerland) at 37° C. using glass silanized vials. Cells were pre-incubated 15 min at 37° C. in presence of test compounds in a concentration range of $10^{-11}$–$10^{-5}$ M or in presence of the same amount (5 μl) of vehicle control (DMSO). Then a mixture of 0.5 nM [$^3$H]-AEA (60 Ci/mmol) (American Radiolabeled Chemicals, Inc., San Louis, Mo., US) and 99.5 nM of nonradioactive AEA (Tocris Cookson Ltd., Bristol, UK) resulting in a final concentration of 100 nM AEA was added and samples were incubated at 37° C. for another 15 minutes. The reaction was stopped by rapid filtration over UniFilter@-96 GF/C (Perkin Elmer, Boston Mass., US) pre-soaked with PBS 0.25% BSA (w/v). Cells were washed three times with ice-cold PBS buffer containing 1% fatty acid free BSA (137 mM NaCl, 2.7 mM KCl, 10 mM $Na_2HPO_4$, 1.76 mM $KH_2PO_4$, 1% BSA fatty acid free, pH 7.4), dried and 40 μl MicroScint 20 scintillation cocktail (Perkin Elmer, Waltham, Mass., US) was added. Radioactivity was measured using a Perkin Elmer 1450 Microbeta TRILUX liquid scintillation counter. Results were expressed as % of AEA uptake versus cells treated with solvent and the $EC_{50}$ and $IC_{50}$ values were calculated from the sigmoidal curves, which were generated using the GraphPad Prism 5.0 (GraphPad Software, San Diego, Calif., US).

TABLE 2

Inhibition of Arachidonoylethanolamide Transport (AEAT)
(Determination as Described in Biological Assays C)

| Example | AEAT uptake at 250 nM % of control | AEAT uptake at 1 μM % of control | AEAT $EC_{50}$ (nM) |
|---|---|---|---|
| 2 | | | 4.0 |
| 3 | | | 35 |
| 4 | | | 146 |
| 5 | | | 30 |
| 6 | | | 272 |
| 7 | | | 10 |
| 8 | | | 64 |
| 9 | | | 17 |
| 10 | | | 112 |
| 11 | 36 | | |
| 12 | 19 | 6 | |
| 13 | | | 89 |
| 15 | | | 755 |
| 17 | | | 898 |

D. Fatty acid amide hydrolase (FAAH) inhibition

FAAH activity was assessed using pig brain or U937 homogenate according to the method described by Omeir et. al. Arachidonoyl ethanolamide-[1,2-$^{14}$C] as a substrate for anandamide amidase. Life sciences 56, 1999-2005 (1995) and adapted by Fowler et al. Selective inhibition of anandamide cellular uptake versus enzymatic hydrolysis—a difficult issue to handle. European journal of pharmacology 492, 1-11 (2004).

Briefly, 10 μl of vehicle or positive control URB597 (Cayman Chemical, Ann Arbor, Mich., US) resulting a final concentration of 100 nM or of the inhibitor at the adequate concentrations were pre-incubated at 37° C. for 15 min at 450 rpm with 490 μl of diluted pig brain (200 μg per sample) or U937 homogenate (0.63 mg protein per sample corr. $10^6$ U937 cells) in FAAH activity buffer (10 mM Tris-HCl and 1 mM EDTA, pH 8.0, 0.1% w/v fatty acid free BSA (Sigma, San Louis, Mo., US)). A mixture of 0.5 nM [$^3$H]AEA (60 Ci/mmol) and 99.5 nM of nonradioactive AEA resulting in a total concentration of 100 nM AEA was added and incubated for 15 min. Successively, 1 ml of a mixture 1:1 (v/v) of methanol:chloroform was added to each sample and, after vigorous vortexing, aqueous and organic phases were separated by centrifugation at 10,000 rpm for 10 min at 4° C. The radioactivity associated to the [$^3$H]-ethanolamine (produced by FAAH-catalyzed breakdown of [$^3$H]-AEA) was measured upon addition of 3 ml of Ultima Gold scintillation liquid (Perkin Elmer, Waltham, Mass., US) to the aqueous (upper) phase, using a PACKARD TRI-CARB 2100TR Liquid Scintillation Analyzer. Results were expressed as % of FAAH activity vs. vehicle treated homogenate. Collected data was normalized by subtraction of unspecific signal at total inhibition of FAAH by URB597. Single values of FAAH inhibition or $IC_{50}$ values from generated sigmoidal curves were calculated using GraphPad Prism 5.0 (GraphPad Software, San Diego, Calif., US).

E. Monoacylglycerol lipase (MAGL) inhibition

MAGL activity was evaluated using the Monoacylglycerol Lipase Inhibitor Screening Assay Kit (Cayman Chemicals, Mich., US) and the experimental procedure was carried out according to the kit protocol. Briefly, 10 μl of test compounds at different concentrations (range 0.1-20 μM) were added to 150 μl of assay buffer, 10 μl of human recombinant MAGL and 10 μl of arachidonoyl-1-thio-glycerol (150 μM in the assay). The plate was incubated at room temperature for 5 min, afterward 10 μl of DTNB (5,5'-dithiobis-(2-nitrobenzoic acid), Ellman's reagent) was added to each well. The plate was shaken for 10 seconds and the absorbance measured at 415 nm using Genius Pro spectrofluorimeter (Tecan, Grodig, Austria). Initial 100% enzymatic activity was calculated using solvent instead of test compounds, whilst background was measured without the human recombinant enzyme. The blank was subtracted from each value and results were expressed as % of initial enzymatic activity.

F. In Vivo Model for Pruritus Associated with the Oxazolone Model of a Delayed Type Hypersensitivity Reaction Scratching activity in mice is measured after topical application of the test compound. Ear thickness is measured and histology parameters are determined (see e.g. Elliott G. R. An automated method for registering and quantifying scratching activity in mice: use for drug evaluation. J. Pharmacol. Toxicol. Methods. 2000; 44:453-459 and Gijbels M. J. Therapeutic interventions in mice with chronic proliferative dermatitis (cpdm/cpdm). Exp. Dermatol. 2000; 9:351-358).

Examples of a Pharmaceutical Composition

Composition Example 9

| Cream | |
|---|---|
| Compound Example 9 | 1.00 |
| Cetostearyl alcohol | 7.00 |
| Macrogol-6-cetostearyl ether | 1.50 |
| Macrogol-25-cetostearyl ether | 1.50 |
| Liquid paraffin | 12.00 |
| Propylene glycol | 8.00 |
| Methylparaben | 0.15 |
| Ethylparaben | 0.08 |
| Butylhydroxytoluene | 0.04 |
| Disodium edetate | 0.05 |
| Water | 68.68 |

Composition Example 7

| Gel | |
|---|---|
| Compound Example 7 | 0.50 |
| Ethanol | 15.00 |
| Polyoxyl 40 Hydrogenated Castor Oil | 1.00 |
| Butylhydroxytoluene | 0.04 |
| Disodium edetate | 0.05 |
| Carbomer | 0.50 |
| Triethanolamine | 0.70 |
| Water | 82.21 |

INDUSTRIAL APPLICABILITY

Utility

The above results clearly show the improved technical effects provided by the 1,3-benzoxazol-2(3H)-one compounds of the present invention. It has surprisingly been found out by the present inventors that these compounds are suitable as active ingredients in pharmaceutical and cosmetic compositions, preferably dermatologic agents. Moreover, the compounds have shown to be effective in treating and/or preventing several diseases and conditions including, but not limited to inflammation, irritation, itching, pruritus, pain, oedema, and/or pro-allergic or allergic conditions, in particular when they are topically applied to the skin or mucosa in the form of pharmaceutical or cosmetic compositions containing a suitable carrier, preferably an apolar carrier. In particular, inflammation induced by cellular stress signals can effectively be attenuated by these compounds. Moreover, the compounds of the invention are effective in the treatment/prevention of hair growth conditions (e.g. alopecia, effluvium), sebaceous gland disorders (e.g. acne, seborrhea), benign and malignant skin tumors, hyperproliferative skin diseases (e.g. psoriasis), excessive hair growth (e.g. hirsutism), different forms of dermatitis, dry skin conditions and/or systemic sclerosis (e.g. *scleroderma*). The compounds of formulae (1) and/or (2) are modulators of the endocannabinoid system and as such are useful in the treatment, control or prevention of the above mentioned diseases, disorders or conditions being responsive to one or more constituents of the endocannabinoid system including, but not limited to $CB_1$ and $CB_2$, TRPV1, GPR55, FAAH, monoacylglyceol lipase (MAGL) or AEAT. The pharmaceutical (dermatological) compositions and preparations containing the compounds of the present invention are highly active, even if the amount of active compound is reduced as compared to prior art compounds, and show less undesirable side-effects.

While the invention has been described and illustrated in reference to certain preferred embodiments thereof, those skilled in the art will appreciate that various changes, modifications and substitutions can be made therein without departing from the spirit and the scope of the invention. For example, effective dosages, other than the preferred doses as set forth above, may be applicable as a consequence of the specific pharmacological responses observed and may vary depending upon the particular active compound selected, as well as from the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

The invention claimed is:

1. A compound of formula (1)

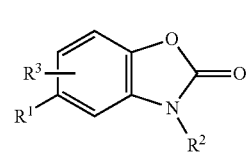

formula (1)

and the enantiomers, diastereomers, tautomers, solvates and pharmaceutically acceptable salts thereof,
wherein
$R^1$ is selected from the group consisting of
—$(CH_2)_n N(R^4)C(O)R^5$ and
—$C(O)NR^4R^6$;
$R^2$ is selected from the group consisting of
hydrogen,
—$C_{1-6}$-alkyl,
—$C_{3-7}$cycloalkyl, and
—$(C_{3-7}$cycloalkyl)-$C_{1-6}$-alkyl;
$R^3$ is hydrogen, halogen, hydroxy, methoxy or —CN;
$R^4$ is hydrogen or $C_{1-6}$-alkyl;
$R^5$ is selected from $C_{8-15}$alkyl, $C_{8-15}$alkenyl, $C_{8-15}$alkinyl, $(C_{6-10}$aryl)-$C_{6-10}$alkyl, $(C_{6-10}$aryl)-$C_{6-10}$alkenyl, and $(C_{6-10}$aryl)-$C_{6-10}$alkinyl;
$R^6$ is selected from $C_{9-16}$alkyl, $C_{9-16}$alkenyl, $C_{9-16}$alkinyl, $(C_{6-10}$aryl)-$C_{7-11}$alkyl, $(C_{6-10}$aryl)-$C_{7-11}$alkenyl, and $(C_{6-10}$aryl)-$C_{7-11}$alkinyl; and,
n is 0, 1, or 2.

2. The compound according to claim 1, wherein in formula (1)
$R^1$ is —$(CH_2)_m N(R^4)C(O)R^5$, wherein n is 0 or 1;
$R^2$ is hydrogen or $C_{1-6}$alkyl,
$R^3$ is hydrogen or halogen;
$R^4$ is hydrogen; and
$R^5$ is selected from $C_{8-15}$alkyl, $C_{8-15}$alkenyl, $(C_{6-10}$aryl)-$C_{6-10}$alkyl, and $(C_{6-10}$aryl)-$C_{6-10}$alkenyl.

3. The compound according to claim 1, wherein in formula (1)
$R^1$ is —$C(O)NR^4R^6$;
$R^2$ is hydrogen or $C_{1-6}$alkyl;
$R^3$ is hydrogen or halogen;
$R^4$ is hydrogen; and
$R^6$ is selected from $C_{9-16}$alkyl, $C_{9-16}$alkenyl, $(C_{6-10}$aryl)-$C_{7-11}$alkyl, and $(C_{6-10}$aryl)-$C_{7-11}$alkenyl.

4. The compound according to claim 1, wherein
$R^1$ is —$(CH_2)_n N(R^4)C(O)R^5$, wherein n is 0;
$R^2$ is hydrogen or methyl;
$R^3$ is hydrogen;
$R^4$ is hydrogen; and
$R^5$ is selected from $C_{8-15}$alkyl, $C_{8-15}$alkenyl having 1, 2, or 3 double bonds, $(C_{6-10}$aryl)-$C_{6-10}$alkyl, and $(C_{6-10}$aryl)-$C_{6-10}$alkenyl having 1 or 2 double bonds.

5. The compound according to claim 1, wherein in formula (1)
$R^1$ is —$C(O)NR^4R^6$;
$R^2$ is hydrogen or methyl;
$R^3$ is hydrogen;
$R^4$ is hydrogen; and
$R^6$ is selected from $C_{9-16}$alkyl, $C_{9-16}$ alkenyl having 1, 2, or 3 double bonds, $(C_{6-10}$aryl)-$C_{7-11}$alkyl, and $(C_{6-10}$aryl)-$C_{7-11}$alkenyl having 1 or 2 double bonds.

6. The compound according to claim 1, wherein
$R^1$ is —$(CH_2)_n N(R^4)C(O)R^5$, wherein n is 0;
$R^2$ is hydrogen or methyl;
$R^3$ is hydrogen;
$R^4$ is hydrogen; and
$R^5$ is selected from $C_{8-12}$alkyl, $C_{8-12}$alkenyl having 2 double bonds, $(C_{6-10}$aryl)-$C_{6-8}$alkyl, and $(C_{6-10}$ aryl)-$C_{6-8}$alkenyl having 2 double bonds.

7. The compound according claim 6, wherein
$R^5$ is selected from $C_{8-12}$alkyl, $C_{8-12}$alkenyl containing a (2E,4E)-diene moiety, $(C_{6-10}$aryl)-$C_{6-8}$ alkyl, and $(C_{6-10}$aryl)-$C_{6-8}$alkenyl containing a (2E,4E)-diene moiety.

8. The compound according to claim 1, wherein in formula (1)
$R^1$ is —$C(O)NR^4R^6$;
$R^2$ is hydrogen or methyl;
$R^3$ is hydrogen;
$R^4$ is hydrogen; and
$R^6$ is selected from $C_{9-13}$alkyl, $C_{9-13}$alkenyl having 2 double bonds, $(C_{6-10}$aryl)-$C_{7-9}$alkyl, and $(C_{6-10}$ aryl)-$C_{7-9}$alkenyl having 2 double bonds.

9. The compound according to claim 8, wherein
$R^6$ is selected from $C_{9-13}$alkyl, $C_{9-13}$alkenyl containing a (2E,4E)-diene moiety, $(C_{6-10}$aryl)-$C_{7-9}$ alkyl, and $(C_{6-10}$ aryl)-$C_{7-9}$alkenyl containing a (2E,4E)-diene moiety.

10. The compound according to claim 1 for use as a medicament.

11. The compound according to claim 1 for use in treating or preventing at least one of following: inflammation, irritation, itching, pruritus, pain, oedema, pro-allergic or allergic conditions, alopecia, effluvium, sebaceous gland disorders, benign and malignant skin tumors, hyperproliferative skin diseases, excessive hair growth, dermatitis, dry skin conditions, and systemic sclerosis.

12. The compound according to claim 1 which is applied topically on the skin or mucosa of a mammal.

13. Non-therapeutic use of the compound as defined in claim 1 as a cosmetic.

14. Non-therapeutic use according to claim 13 for at least one of the following: reducing inflammation, irritation, itching, pruritus, pain, oedema, pro-allergic or allergic conditions, alopecia, effluvium, sebaceous gland disorders, hyperproliferative skin diseases, excessive hair growth, dermatitis, dry skin conditions, and systemic sclerosis.

15. Composition comprising the compound as defined in claim 1 and a pharmaceutically or cosmetically acceptable carrier, wherein the composition is a liniment, skin cream, gel, or lotion.

16. The compound of claim 1, wherein $R^2$ is selected from the group consisting of hydrogen, —$C_{1-6}$alkyl, substituted with one or more substituents selected from halogen, OH, $OC_{1-6}$alkyl, $OC_{3-7}$cycloalkyl; —$C_{3-7}$cycloalkyl, substituted with one or more substituents selected from halogen, OH, $OC_{1-6}$alkyl, and $OC_{3-7}$cycloalkyl; and —$(C_{3-7}$cycloalkyl)-$C_{1-6}$-alkyl, substituted with one or more substituents selected from halogen, OH, $OC_{1-6}$alkyl, and $OC_{3-7}$cycloalkyl.

17. The compound of claim 2, wherein $R^2$ is hydrogen or $C_{1-6}$alkyl, substituted with one or more substituents selected from halogen, OH, $OC_{1-6}$alkyl, $OC_{3-7}$cycloalkyl; $R^3$ is hydrogen; and $R^5$ is selected from $C_{8-15}$alkyl, $C_{8-15}$alkenyl, $(C_{6-10}$ aryl)-$C_{6-10}$alkyl, and $(C_{6-10}$aryl)-$C_{6-10}$alkenyl, wherein aryl is substituted.

18. The compound of claim 3, wherein $R^2$ is hydrogen or $C_{1-6}$alkyl, substituted with one or more substituents selected from halogen, OH, $OC_{1-6}$alkyl, $OC_{3-7}$cycloalkyl; $R^3$ is hydrogen; and $R^6$ is selected from $C_{9-16}$alkyl, $C_{9-16}$alkenyl, $(C_{6-10}$ aryl)-$C_{7-11}$alkyl, and $(C_{6-10}$aryl)-$C_{7-11}$ alkenyl, wherein aryl is substituted.

* * * * *